(12) United States Patent
White

(10) Patent No.: US 10,980,693 B2
(45) Date of Patent: Apr. 20, 2021

(54) MODULAR PATIENT POSITIONING SYSTEM

(71) Applicant: White Surgical Incorporated, Fort Wayne, IN (US)

(72) Inventor: Stephen Edward White, Fort Wayne, IN (US)

(73) Assignee: White Surgical Incorporated, Fort Wayne, IN (US)

( * ) Notice: Subject to any disclaimer, the term of this patent is extended or adjusted under 35 U.S.C. 154(b) by 624 days.

(21) Appl. No.: 15/386,290

(22) Filed: Dec. 21, 2016

(65) Prior Publication Data

US 2017/0216122 A1     Aug. 3, 2017

Related U.S. Application Data

(63) Continuation-in-part of application No. 15/015,109, filed on Feb. 3, 2016, now abandoned.

(51) Int. Cl.
*A61G 13/12* (2006.01)
*A61B 6/04* (2006.01)

(52) U.S. Cl.
CPC ........ *A61G 13/1245* (2013.01); *A61B 6/0407* (2013.01); *A61B 6/0421* (2013.01); *A61G 13/126* (2013.01); *A61G 13/1285* (2013.01); *A61G 13/1295* (2013.01)

(58) Field of Classification Search
CPC .... A61B 6/0421; A61B 6/0407; A61G 7/015; A61G 7/065; A61G 7/075; A61G 7/0755; A61G 13/0036; A61G 13/0063; A61G 13/0072; A61G 13/0081; A61G 13/08; A61G 13/12; A61G 13/121; A61G 13/122; A61G 13/1225; A61G 13/123; A61G 13/1245; A61G 13/126; A61G 13/1285; A61G 13/129; A61G 13/1295
See application file for complete search history.

(56) References Cited

U.S. PATENT DOCUMENTS

| | | | |
|---|---|---|---|
| 516,587 | A | 3/1894 | Campbell |
| 2,678,857 | A | 5/1954 | Hanns |
| 3,931,654 | A | 1/1976 | Spann |
| 3,938,205 | A | 2/1976 | Spann |
| 3,967,128 | A * | 6/1976 | Smulewicz .......... A61B 6/0421 378/174 |

(Continued)

*Primary Examiner* — Nicholas F Polito
(74) *Attorney, Agent, or Firm* — Taylor IP, P.C.

(57) ABSTRACT

During orthopedic surgeries, body parts are moved in different ways to cause different anatomic features (e.g. muscles or the trochanters) to tighten or loosen, or become more or less prominent during the intended surgical incisions, which can result in easier surgical procedures. Body parts can be moved using a variety of different structures. The exemplary structures described herein can allow for: (1) a person's leg and foot to be rotated about the axis of the leg (i.e., femur/tibia axis); (2) a person's leg can be pivoted generally about the hip/femoral head/acetabulum to vary the angle between the axis of the leg and a median sagittal plane; (3) a person's leg can be moved in a direction parallel to the leg axis; and/or a person's leg can be pivoted in a generally vertical plane, about the femoral head/acetabulum while the axis of the leg and the median sagittal plane remaining substantially parallel.

7 Claims, 35 Drawing Sheets

(56) References Cited

U.S. PATENT DOCUMENTS

| | | | | |
|---|---|---|---|---|
| 4,526,355 | A * | 7/1985 | Moore | A61G 13/0063 5/624 |
| 4,624,245 | A | 2/1986 | Mullin | |
| 4,635,306 | A | 1/1987 | Willey | |
| 5,056,535 | A * | 10/1991 | Bonnell | A61G 13/12 128/882 |
| 5,096,173 | A | 3/1992 | Yamashita | |
| 5,289,603 | A | 3/1994 | Kumagai | |
| 5,353,809 | A * | 10/1994 | Faucher | A61B 6/0421 128/878 |
| 5,484,393 | A | 1/1996 | McCoy | |
| 5,568,664 | A | 10/1996 | Lin | |
| 5,832,550 | A | 11/1998 | Hauger | |
| 5,862,551 | A * | 1/1999 | Oguma | A61G 7/015 403/231 |
| 5,941,175 | A * | 8/1999 | Bannister | A61G 13/1245 108/20 |
| 6,032,669 | A | 3/2000 | Klein | |
| 6,202,230 | B1 * | 3/2001 | Borders | A61G 13/0009 5/613 |
| 6,305,039 | B1 | 10/2001 | Jenkins | |
| 6,378,149 | B1 * | 4/2002 | Sanders | A61B 6/0442 378/209 |
| 6,398,409 | B1 | 6/2002 | Brooks | |
| 6,553,995 | B1 | 4/2003 | Cole | |
| 6,564,406 | B2 | 5/2003 | Van Steenburg | |
| 6,622,727 | B2 | 9/2003 | Perry | |
| 6,934,987 | B2 | 9/2005 | Newkirk | |
| 6,941,951 | B2 | 9/2005 | Huburt | |
| 7,100,225 | B1 | 9/2006 | Bailey | |
| D553,751 | S | 10/2007 | Penenberg | |
| 7,415,741 | B1 | 8/2008 | Wasley | |
| 7,694,369 | B2 | 4/2010 | Hinders | |
| 7,836,890 | B2 | 11/2010 | Waternab | |
| 8,336,554 | B1 * | 12/2012 | Williams | A61F 5/0116 128/845 |
| D731,832 | S | 6/2015 | Feiner | |
| 9,216,124 | B2 * | 12/2015 | Spendley | A61G 13/08 |
| 2003/0167569 | A1 * | 9/2003 | Newkirk | A61G 13/12 5/613 |
| 2004/0093673 | A1 | 5/2004 | Marshall | |
| 2004/0133979 | A1 | 7/2004 | Newkirk | |
| 2004/0201917 | A1 | 10/2004 | Pierson | |
| 2005/0085722 | A1 * | 4/2005 | Waterman | A47C 20/027 600/427 |
| 2007/0089239 | A1 | 4/2007 | Whiteside | |
| 2009/0012437 | A1 * | 1/2009 | Tucker | A61F 5/3761 602/19 |
| 2011/0030698 | A1 * | 2/2011 | Kaufman | A61B 5/0555 128/845 |
| 2013/0340167 | A1 * | 12/2013 | Karwal | A61G 7/005 5/611 |
| 2014/0059773 | A1 | 3/2014 | Carn | |
| 2014/0128987 | A1 * | 5/2014 | Kelley | A61F 2/36 623/22.12 |
| 2014/0182062 | A1 | 7/2014 | Aghazadeh | |
| 2015/0305951 | A1 * | 10/2015 | Valentino | A61G 5/12 5/623 |
| 2017/0135891 | A1 * | 5/2017 | Kettner | A61G 13/1295 |

\* cited by examiner

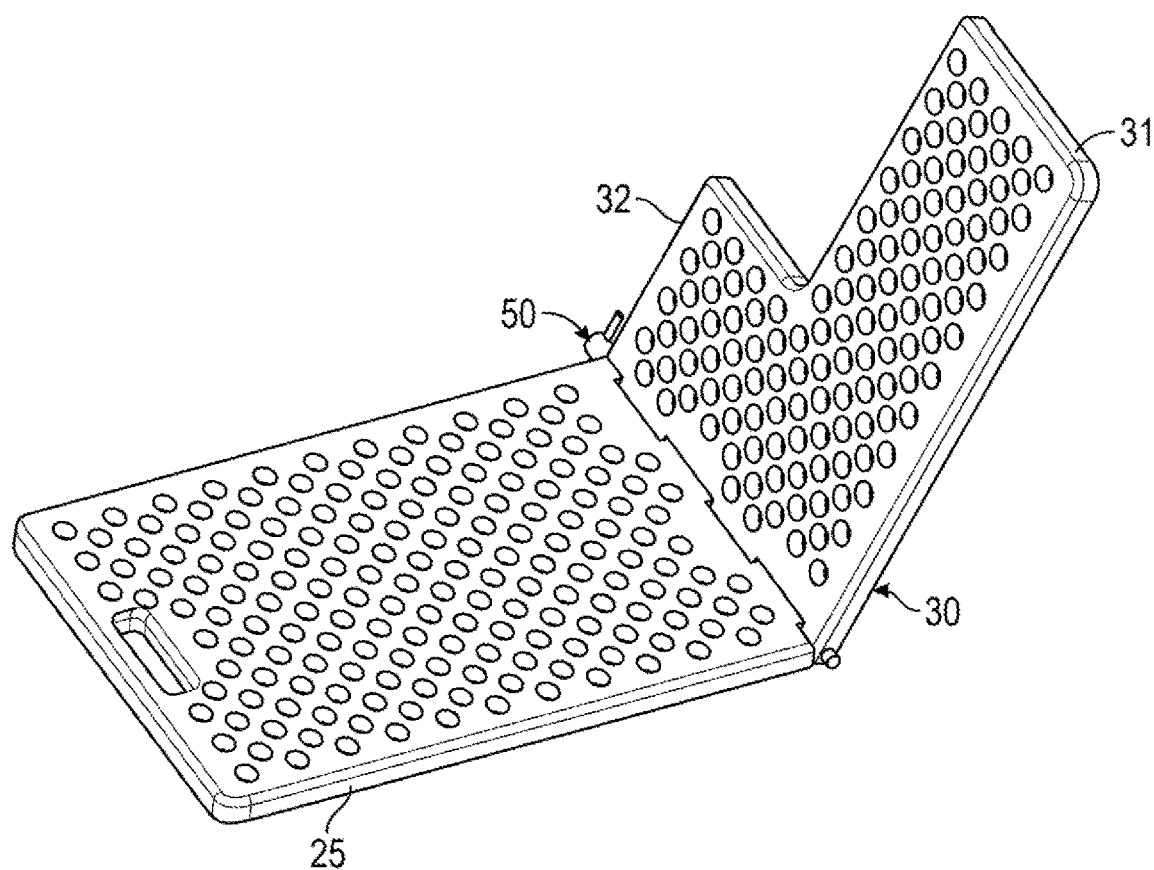
FIG. 6
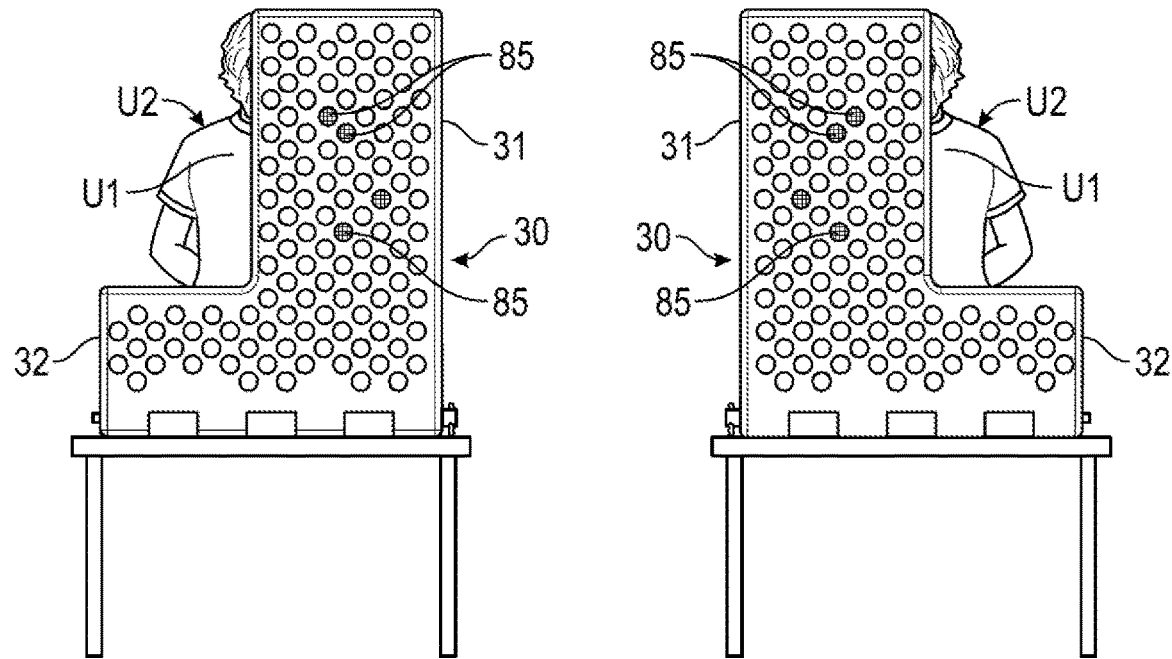
FIG. 7A  FIG. 7B

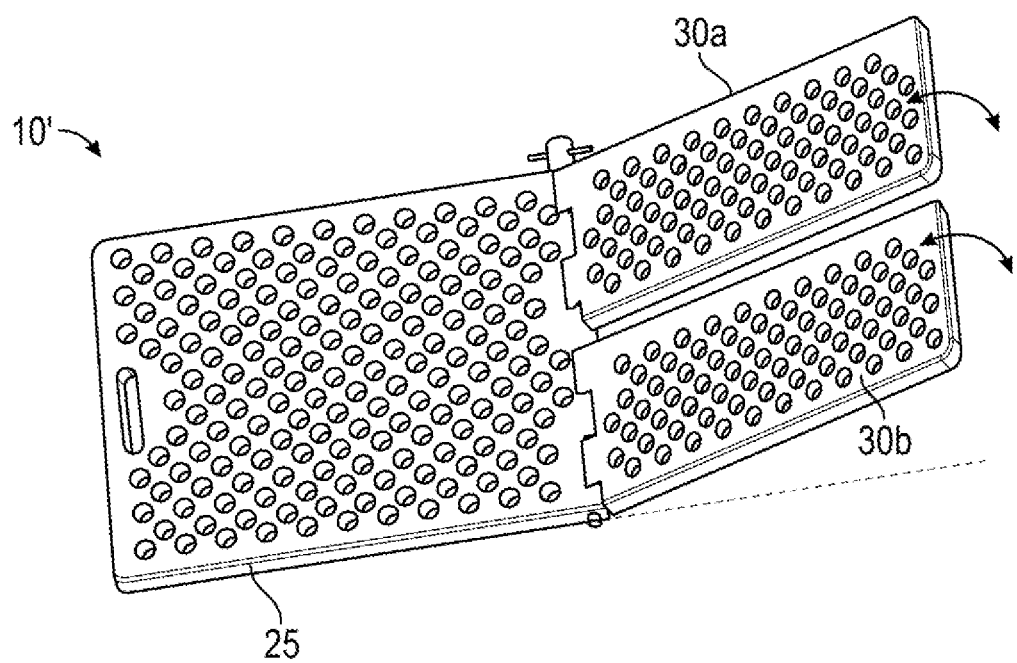
FIG. 20
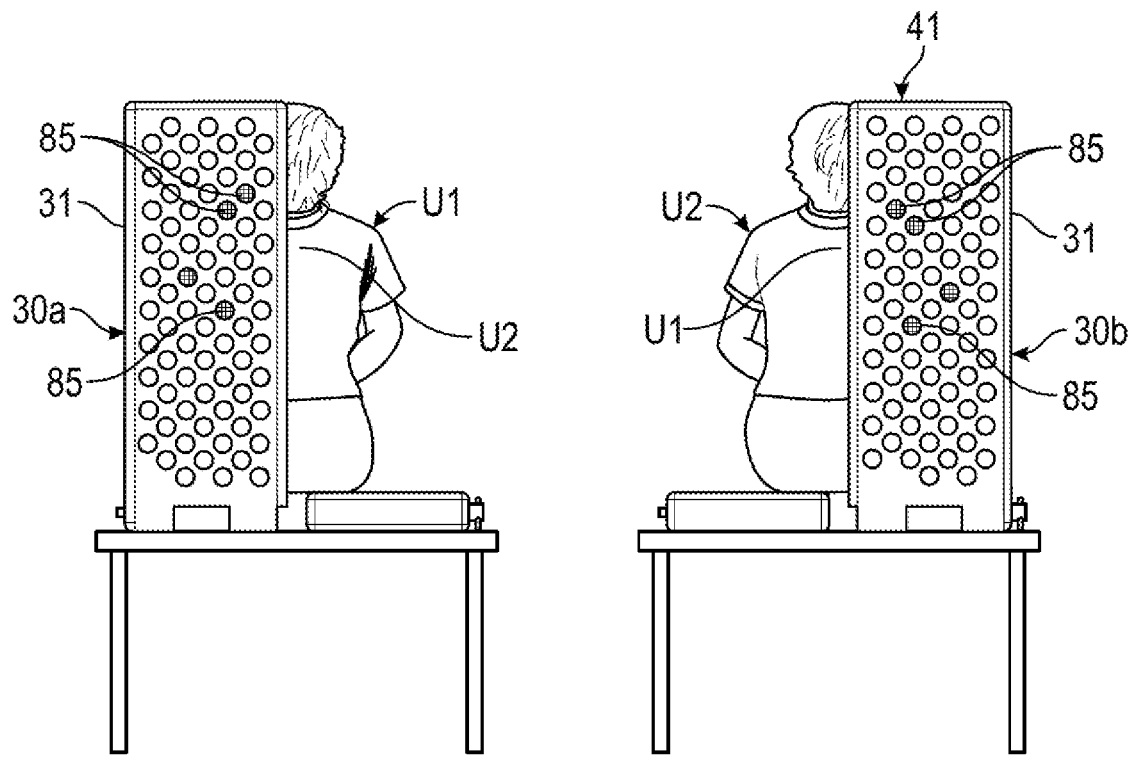
FIG. 21A  FIG. 21B

MODULAR PATIENT POSITIONING SYSTEM

RELATED APPLICATIONS

This application claims priority to co-pending U.S. patent application Ser. No. 15/015,109, filed Feb. 3, 2016, the contents of which are incorporated herein by reference in its entirety.

FIELD OF DISCLOSURE

The disclosure is generally directed to the field of modular patient positioning systems (referred to herein as "MPPS"). In particular, the disclosure is directed to the field of MPPSs for use in orthopedic surgery and conveniently positioning or extending different body portions to be operated upon in different positions. The system of the current disclosure allows surgeons and operating room staff to use a reduced amount of hardware in combination with a foundational device to position, support, and improve the results of the surgical procedure. Moreover, small movements that can cause joint misalignment are preventable with the system. The modularity of the system also allows one system to be used for posterior or anterior hip surgery, knee surgery, extremity surgery, as well as a sit-up position for neck or shoulder surgery. The system also allows for controlling the anatomic positions, such as flexion/extension, abduction and adduction, elevation/depression, rotation and distraction/compression of various joints or bones, such as the hip or knee.

BRIEF DESCRIPTION OF THE DRAWINGS

FIG. 6 shows another embodiment of the MPPS; in this exemplary embodiment, the MPPS is for supporting a first part of the patient's upper body and providing unobstructed access to a second part of the patient's upper body, on which surgery is to be performed.

FIG. 7A, FIG. 7B are rear views, showing how the exemplary embodiment of FIG. 6 allows unobstructed access to either of the left or right side parts of the patient's upper body, on which surgery is to be performed.

FIG. 18D shows the use of a leg positioner for flexing, e.g., a knee, during surgery thereon. FIG. 18E shows peg-using structures for use with a leg positioner to vary the position of the leg positioner and thereby adjust the amount of flexion/extension and/or distraction/compression of at least a portion of the leg.

FIG. 20 shows the exemplary embodiment of the MPPS of FIG. 16A in a configuration for performing surgery on an upper portion of a patient's body.

FIG. 21A and FIG. 21B are rear views similar to those of FIG. 7A and FIG. 7B, respectively, where different portions of the patient's upper body are supported and different portions of the patient's upper body are unobstructed for surgery thereon.

DETAILED DESCRIPTION

Figure 1A:
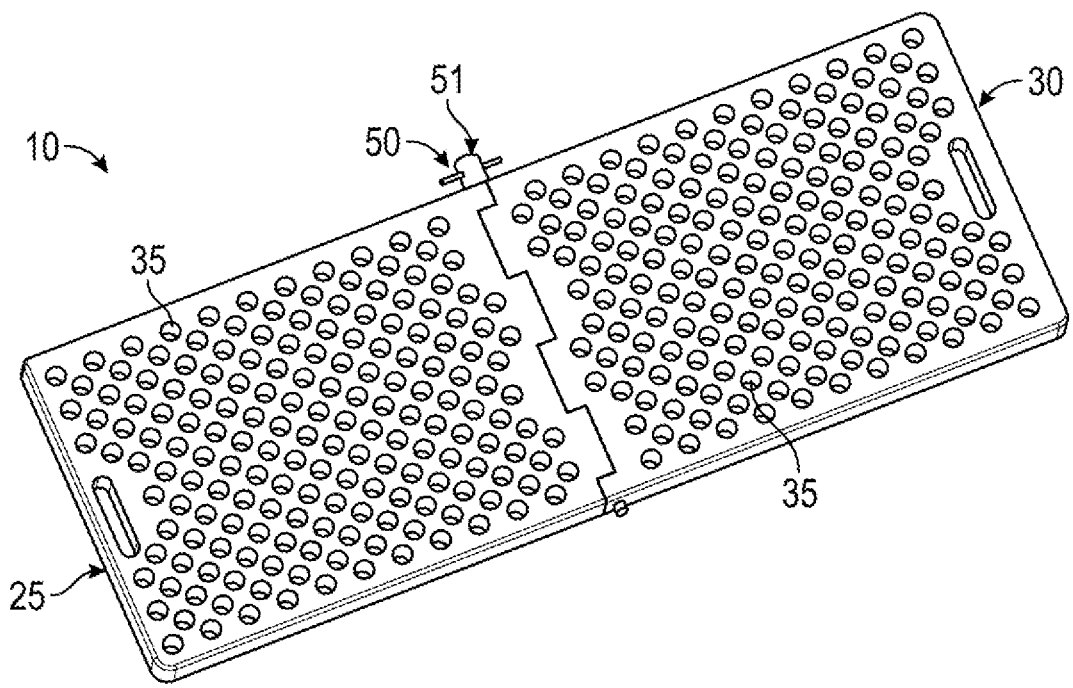
FIG. 1A shows a first exemplary embodiment of an MPPS, which comprises two separate pegboards and in a first configuration.

It will be appreciated that for simplicity and clarity of illustration, numerous specific details are set forth in order to provide a thorough understanding of the embodiments described herein. However, it will be understood by those of ordinary skill in the art that the embodiments described herein can be practiced without these specific details. In other instances, methods, procedures and components have not been described in detail so as not to obscure the related relevant feature being described. Also, the description is not to be considered as limiting the scope of the embodiments described herein. The drawings are not necessarily to scale and the proportions of certain parts have been exaggerated to better illustrate details and features of the present disclosure. Similar reference numerals are used to refer to structures similar to the various exemplary embodiments.

The embodiments shown and described above are only examples. Therefore, many such details are neither shown nor described. Even though numerous characteristics and advantages of the present technology have been set forth in the foregoing description, together with details of the structure and function of the present disclosure, the disclosure is illustrative only, and changes may be made in the detail, especially in decorative and structural matters of shape, size and arrangement of the parts within the principles of the present disclosure up to, and including the full extent established by the broad general meaning of the terms used in the claims. It will therefore be appreciated that the embodiments described above may be modified within the scope of the claims.

During orthopedic surgeries, it can be useful to move different body parts in different ways to cause different anatomic features (e.g. muscles or the trochanters) to, for example: tighten or loosen, become more or less prominent, or "move out of the way" of intended surgical incisions. Body parts can be moved in a variety of ways to achieve different anatomical positionings. Common exemplary terms used to describe anatomical movements include: flexion/extension, abduction and adduction, elevation/depression, rotation, and distraction/compression.

Some various ways in which body parts can be moved will be described with reference to FIG. 23, which shows a person and the median sagittal plane of that person, and FIGS. 24A-D.

Figure 23:
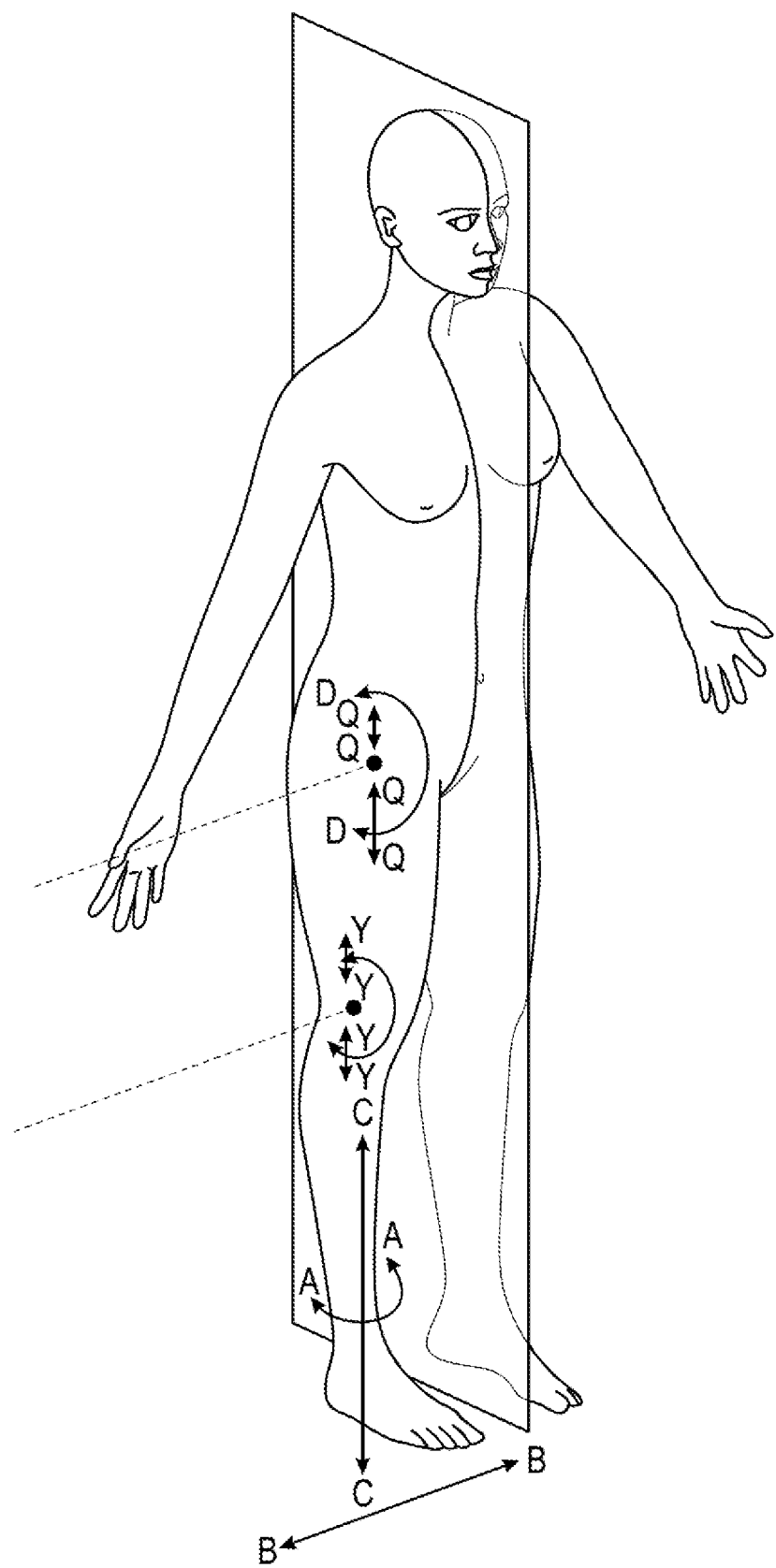
FIG. 23 shows a person, the median sagittal plane of that person, and the various exemplary anatomical directions in which a leg to be operated on can be moved.
Figure 24A:
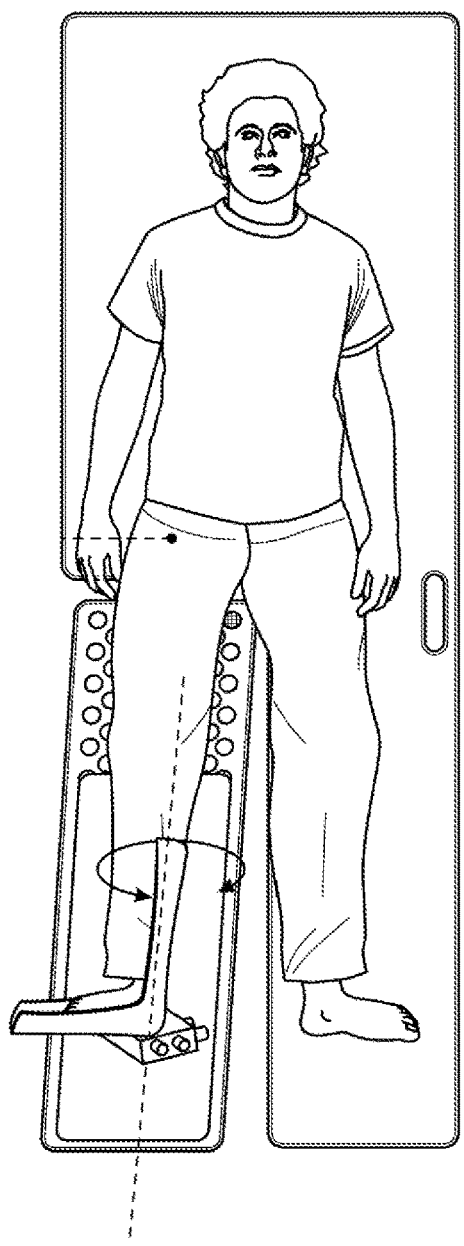
FIG. 24A shows at least one of axial rotation, abduction/adduction, elevation/depression, distraction/compression or flexion/extension of at least a portion of the leg being adjusted.
Figure 24B:
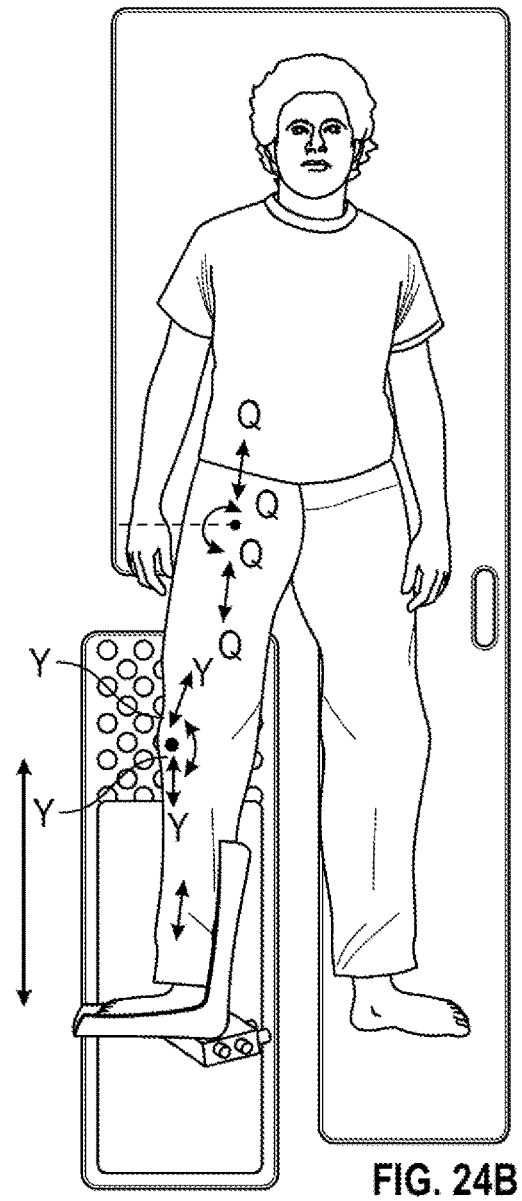
FIG. 24B shows at least two of axial rotation, abduction/adduction, elevation/depression, distraction/compression or flexion/extension of at least a portion of the leg being adjusted.
Figure 24C:
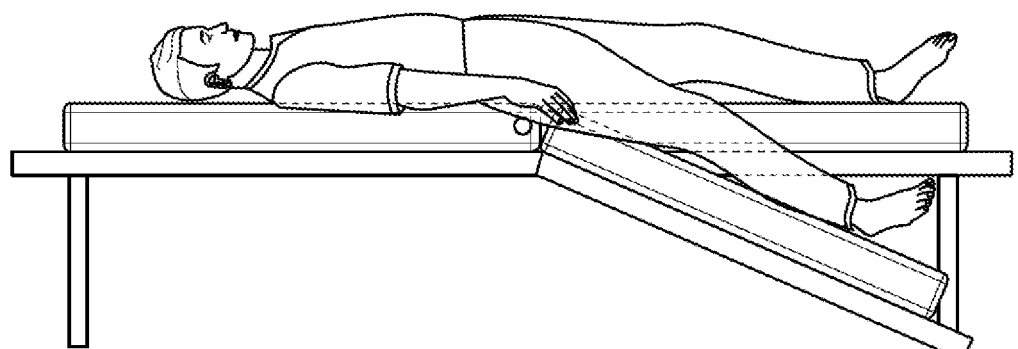
FIG. 24C shows at least three of axial rotation, abduction/adduction, elevation/depression, distraction/compression or flexion/extension of at least a portion of the leg being adjusted.
Figure 24D:
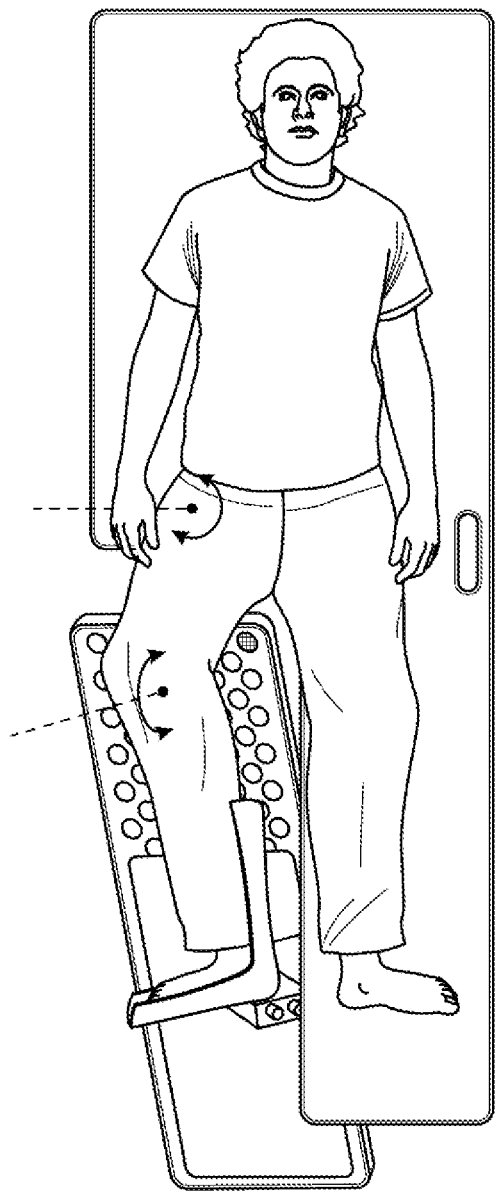
FIG. 24D shows all of axial rotation, abduction/adduction, elevation/depression, distraction/compression or flexion/extension of at least a portion of the leg being adjusted.

As shown by arrow A-A of FIG. 23, a person's leg and thus also the person's foot, can be rotated about the axis of the leg (i.e., femur/tibia axis). As used herein, this type of movement will be called axial rotation.

As shown by arrow B-B of FIG. 23, a person's leg can be pivoted generally about the hip/femoral head/acetabulum), to vary the angle between the axis of the leg (i.e., femur/tibia axis) and the median sagittal plane, resulting in potentially easier surgical procedures. As used herein, this type of movement will be called abduction/adduction.

As shown by arrow C-C of FIG. 23, a person's foot/lower leg (tibia) can be moved in a direction parallel to the leg axis (femur/tibia axis) towards or away from the body trunk. During this type of movement, several other movements may occur, depending up how or whether different body parts are constrained. For example, there can be knee flexion/extension; hip flexion/extension, knee distraction/compression, or knee distraction/compression. When allowing these types of movements, the angle of the femoral head within the acetabulum will change, resulting in potentially easier surgical procedures. As used herein, this type of movement will be called flexion/extension <?>.

As shown by arrow D-D of FIG. 23, a person's leg can be pivoted in a generally vertical plane, about the femoral head/acetabulum axes while the axis of the leg (femur/tibia axis) and the median sagittal plane remaining substantially parallel, resulting in potentially easier surgical procedures. As used herein, this type of movement will be called elevation/depression.

Accordingly, by performing any of the movements described above, the positioning of various anatomical hip features can be made more or less prominent or moved out of the way of surgical incisions, as desired by the surgical method to be used on that patient's hip and resulting in potentially easier surgical procedures.

For example, in a first exemplary embodiment, at least one of axial rotation, abduction/adduction, elevation/depression, distraction/extraction or flexion/extension (see e.g. FIG. 24A) are adjusted.

In a second exemplary embodiment, at least two of axial rotation, abduction/adduction, elevation/depression, distraction/extraction or flexion/extension (see e.g. FIG. 24B) are adjusted.

In a third exemplary embodiment, at least three of axial rotation, abduction/adduction, elevation/depression, distraction/extraction or flexion/extension (see e.g. FIG. 24C) are adjusted.

In a fourth exemplary embodiment, all of axial rotation, abduction/adduction, elevation/depression, distraction/extraction or flexion/extension (see e.g. FIG. 24D) are adjusted.

As used herein, "of the leg" or "a portion of the leg" can comprises any of anatomical features of the leg, including, but not limited to: foot, angle, tibia, fibular, knee, femur, hip and the anatomical features the comprise the angle, knee, and hip joints.

The structure by which these various movements can be carried out are described below.

FIG. 1A shows a first exemplary embodiment of a modular patient positioning system ("MPPS") 10 and in a first configuration. This exemplary embodiment of the MPPS 10 includes at least first pegboard 25 and second pegboard 30. Typically, though not necessarily, the first pegboard 25 and the second pegboard 30 are generally the same size. The first pegboard 25 and the second pegboard 30 have pegboard holes 35 therein, for reasons discussed below. The at least first pegboard 25 and second pegboard 30 may be connected together, such that the first pegboard 25 and second pegboard 30 can be rotated relative to each other between different configurations. In the exemplary embodiment of the MPPS of FIG. 1A; the first pegboard 25 and second pegboard 30 are connected together by a hinge 50. Hinge 50 may comprise a removable hinge pin 51. However, as exemplified in FIG. 16B, hinges are not necessary.

Figure 1B:
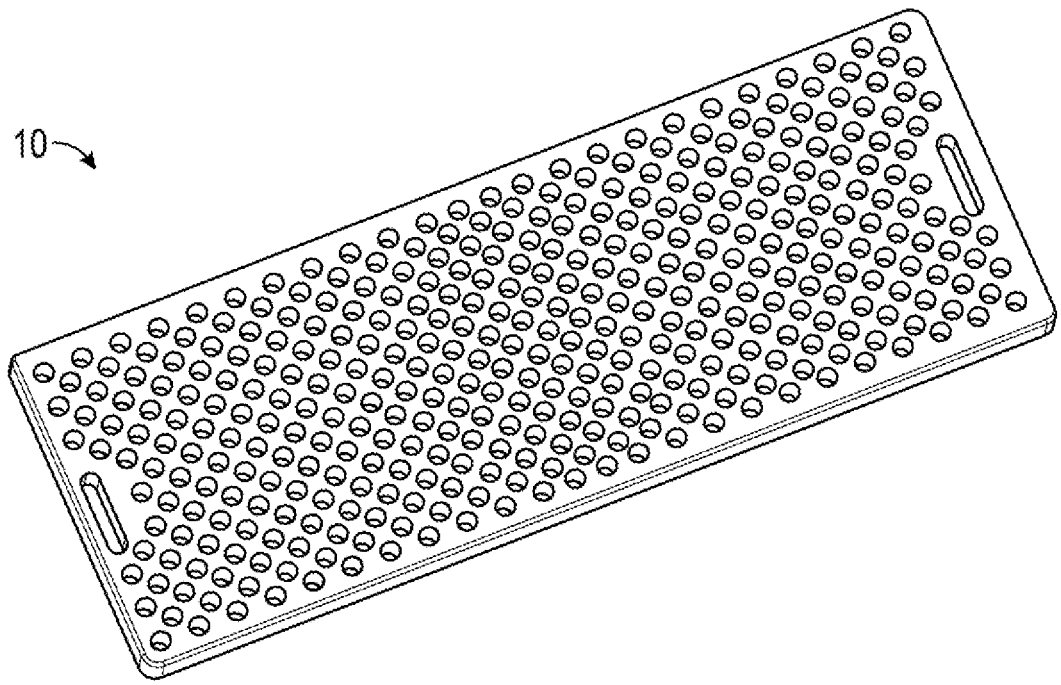
FIG. 1B shows another exemplary embodiment of an MPPS that comprises one pegboard.

In a first configuration, as shown in FIG. 1A, the first pegboard 25 and second pegboard 30 lie along a common plane. In FIG. 1B, the MPPS comprises a single pegboard.

Figure 2:
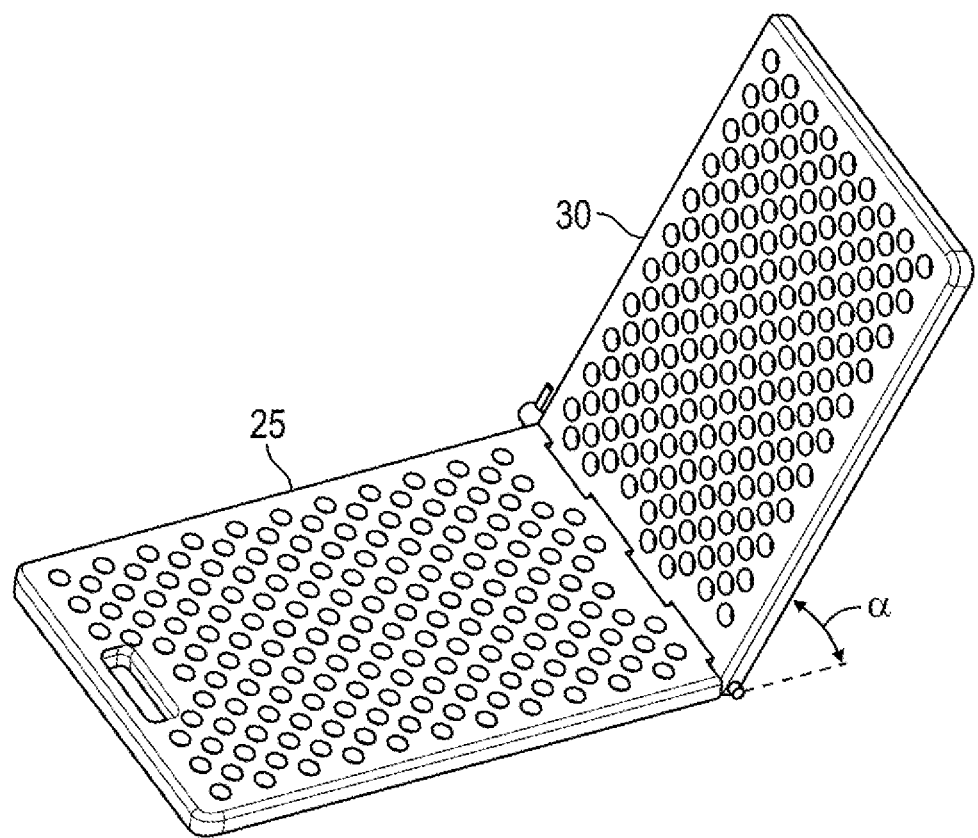
FIG. 2 shows the first exemplary embodiment of the MPPS of FIG. 1A in a second configuration.

In a second configuration, as shown in FIG. 2, the first pegboard 25 and second pegboard 30 lie along different planes at an angle α. The second configuration allows for different parts of a patient's body to be positioned and supported in different planes. The second configuration usually includes one pegboard lying flat (e.g. substantially horizontally) or parallel to a top surface of a surgical table and the other pegboard being at a positive or negative angle α relative to the flat pegboard (see discussions of FIGS. 3A-3C below). For ease of reference and not intended to be limiting in any way, this disclosure will refer to the "second pegboard" as the pegboard that is raised or lowered, as discussed further below.

Figure 3A:
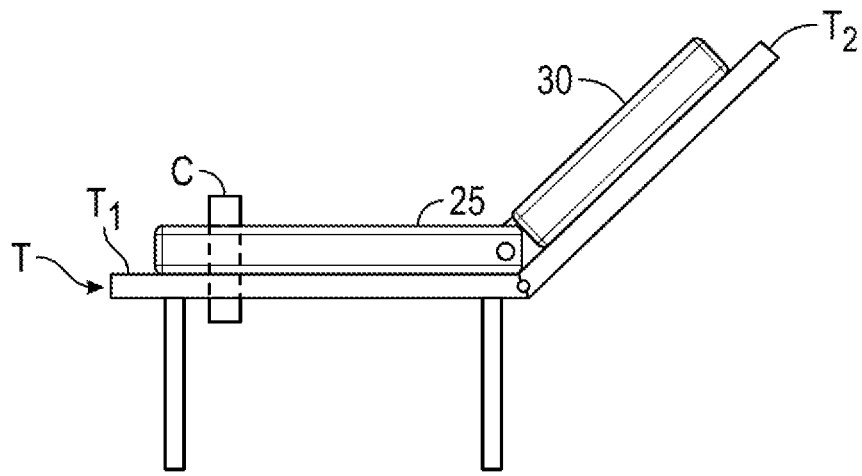
FIG. 3A, FIG. 3B, FIG. 3C show various exemplary ways that the MPPS of FIG. 1A may be used during surgery.
Figure 3B:
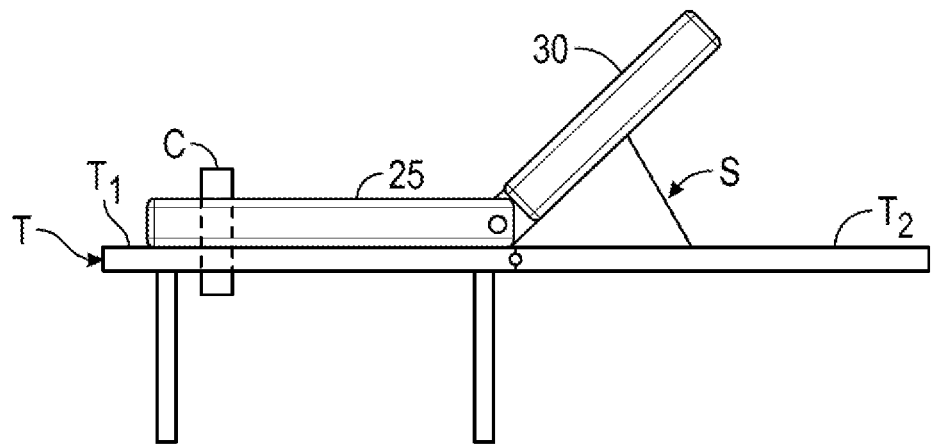
Figure 3C:
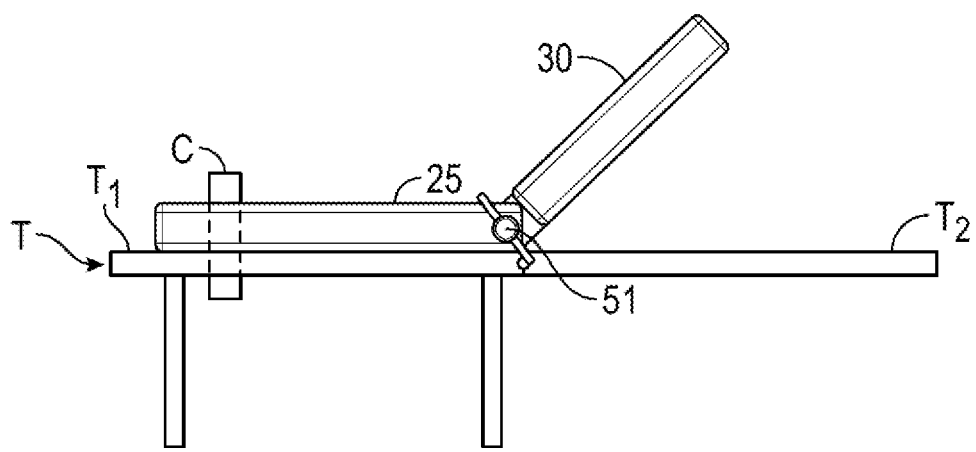

FIGS. 3A-3C show various exemplary ways by which the second pegboard 30 can be supported in a raised position relative to the first pegboard 25.

As shown in FIG. 3A, the MPPS 10 may be supported on (by) a surgical/operating table T (schematically shown). First pegboard 25 may be clamped to a first, typically, fixed-positioned part T1 of the surgical table T by a clamp C. The second pegboard 30 is supported in the raised position by a rotatable portion T2 of the surgical table T and may or may not be clamped to rotatable portion T2.

As shown in FIG. 3B, the MPPS 10 may be supported on (by) a surgical/operating table T (schematically shown). First pegboard 25 may be clamped to a first, typically, fixed-positioned part T1 of the surgical table T by a clamp C. The second pegboard 30 is moved into the raised position and supported in the raised position by a support member S, such as a bar, frame, or wedge, between the top of the surgical table and an underside of the second pegboard 30.

As shown in FIG. 3C, the MPPS 10 may be supported on (by) a surgical/operating table T (schematically shown). First pegboard 25 may be clamped to a first, typically, fixed-positioned part T1 of the surgical table T by a clamp C. The second pegboard 30 is moved into the raised position and supported in the raised position by hinge pin 51 comprising a locking hinge pin.

Figure 4:
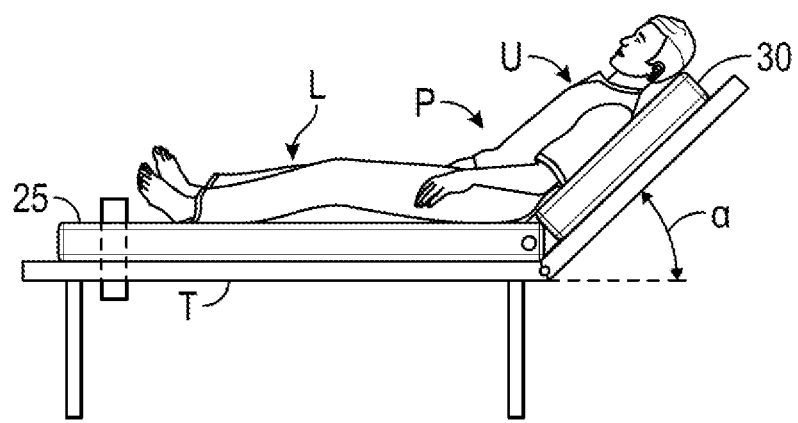
FIG. 4 shows how when the MPPS of FIG. 1A is in the second configuration, the patient's upper body is in a raised position that makes surgery on the upper portion of the patient's upper body easier.

The ability for the first pegboard 25 and second pegboard 30 to rotate relative to each other and receive pads/cushions and pegs makes it easier for a doctor to position different patient's in different body positions using pegs, pegboards, and pads to perform surgery on, for example, upper portions U of a patient's body P. For example, as shown in FIG. 4, when the MPPS is in the second configuration: the first pegboard 25 lies substantially flat on a surgical table T and the second pegboard 30 is rotated upward and away from the plane of the first pegboard 25. In this second configuration, the patient's lower body L lies generally flat on the first pegboard 25 substantially parallel with the surgical table T and the patient's upper body U is supported at a raised angle α above the plane of the first pegboard, to present the patient's upper body U in a raised position that makes surgery on an upper portion U of the patient's upper body U easier.

Thus, when the part of the patient's upper body U to be operated on comprises a shoulder, a doctor may use pads/cushions and pegs (see discussion about FIGS. 5B, 5B, below) to specifically position different patient's in different body positions using pegs. This reduces doctor fatigue during the surgical procedure and maintains desired patient positioning.

The angle α at which the second pegboard supports the patient's upper body relative to the plane of the first pegboard can vary, but generally depends on the heights of the surgical table and the doctor, so that the area of the patient to be operated on is at a position where the surgeon need not lean over the patient, stand in any awkward postures, etc.

Figure 5A:
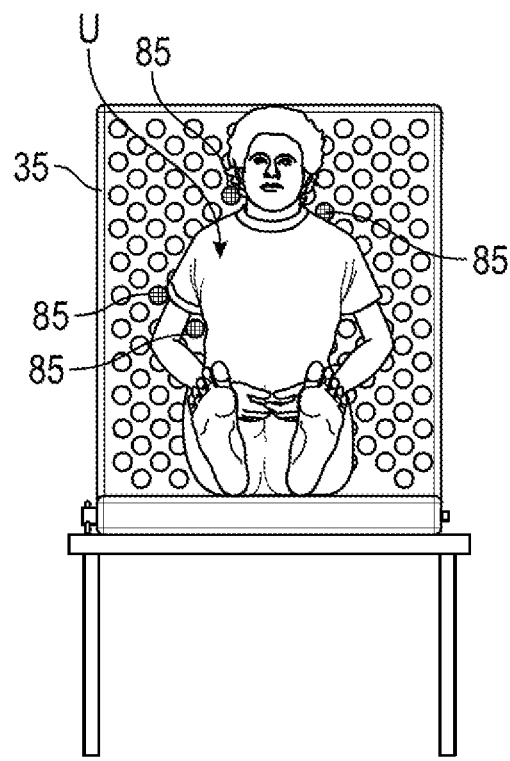
FIG. 5A and FIG. 5B show other exemplary embodiments of an MPPS; in these exemplary embodiments, pegs are shown for retaining a portion of a patient's body in an operating position. The embodiment of FIG. 5A is wider than the embodiment of FIG. 5B.
Figure 5B:
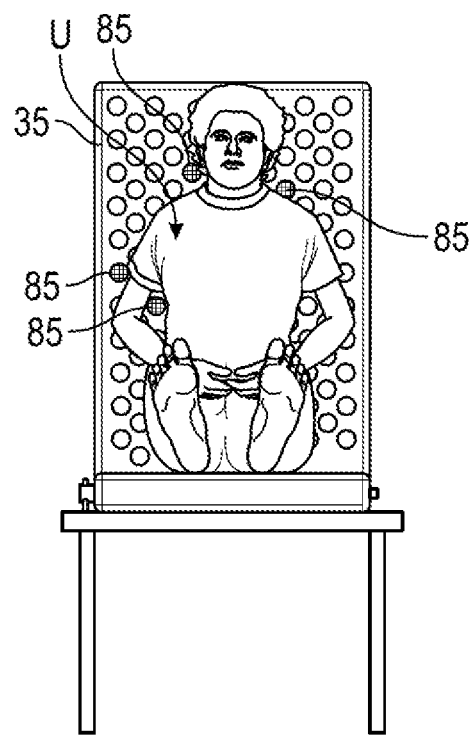

As shown in FIG. 5A and FIG. 5B, one or more pegs 85 may be inserted into pegboard holes 35 and protrude outwardly to retain a portion of the patient's upper body U in a desired surgical position.

As shown in the exemplary embodiment of FIG. 1, the first pegboard 25 and second pegboard 30 are generally identical in structure, allowing ease of installation and replacement of broken parts. However, the first pegboard 25 and second pegboard 30 need not be identical in structure.

For example, as shown in FIG. 6, the second pegboard 30 is L-shaped having a narrow portion 31 and a wide portion 32. Wide portion 32 includes the hinge portion of second pegboard 30. The first pegboard 25 is generally rectangular and equal in width to the wide portion 32 of the second pegboard 30. Thus, the hinge portion of wide portion 32 of the second pegboard 30 can be conveniently connected to the hinge portion of the first pegboard 25 by the hinge pin 51.

As shown in the rear views of FIG. 7A and FIG. 7B, the narrow portion 31 of the second pegboard 30 supports a first part of the patient's upper body U1 and provides unobstructed access to a second part of the patient's upper body U2, on which surgery is to be performed. For example, as shown in rear view FIG. 7A, the patient's left shoulder is supported by narrow portion 31 of the second pegboard 30 and the patient's right shoulder is unobstructed for surgery. As shown in rear view FIG. 7B, the second, L-shaped pegboard may be disconnected from the first pegboard, reversed in configuration, and then reconnected to the first pegboard, whereby the second, L-shaped pegboard may be positioned to provide unobstructed access to the left side of the patient's upper body.

MPPS 10 can be used to raise or lower a patient's legs for surgery thereon, rather than the upper body by merely reversing the positioning of the first pegboard portion and the second pegboard portion. This is described in more detail below. For example, as described below, raising or lowering the second pegboard portion can be used to flex or relax a patient's knee or hip.

Figure 8:
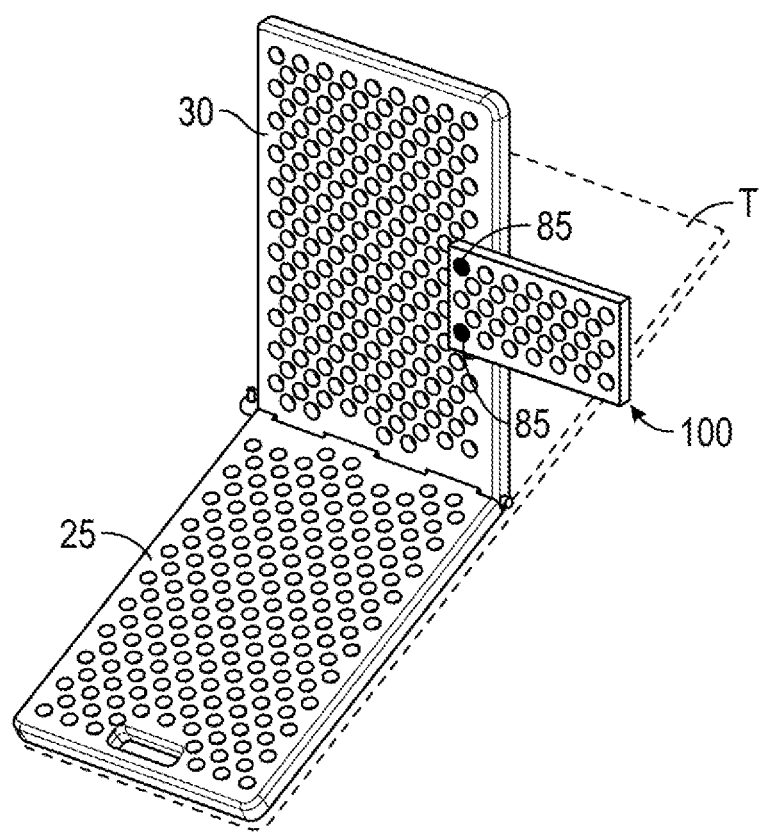
FIG. 8 shows another exemplary embodiment of the MPPS; in this exemplary embodiment, an arm pegboard extends outwardly beyond side edges of a second pegboard and a surgical table.
Figure 10A:
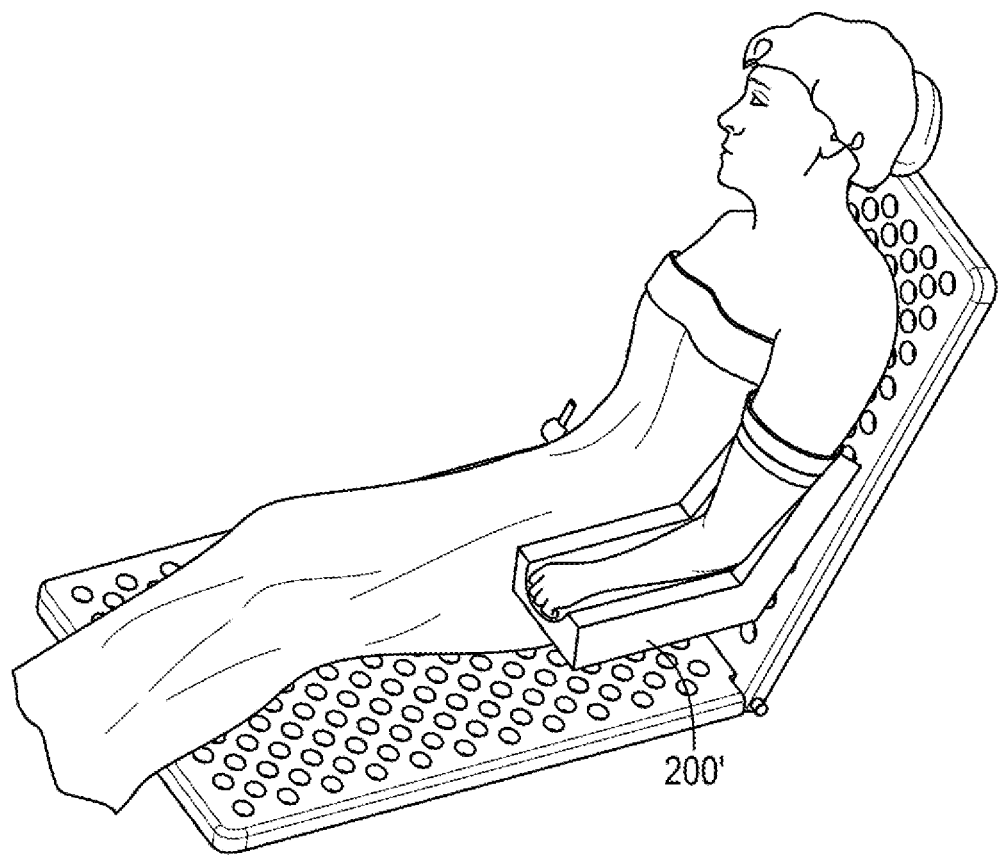
FIG. 10A and FIG. 10B show examples of performing arm surgeries with the exemplary embodiments of FIG. 2 and FIG. 8 respectively.
Figure 10B:
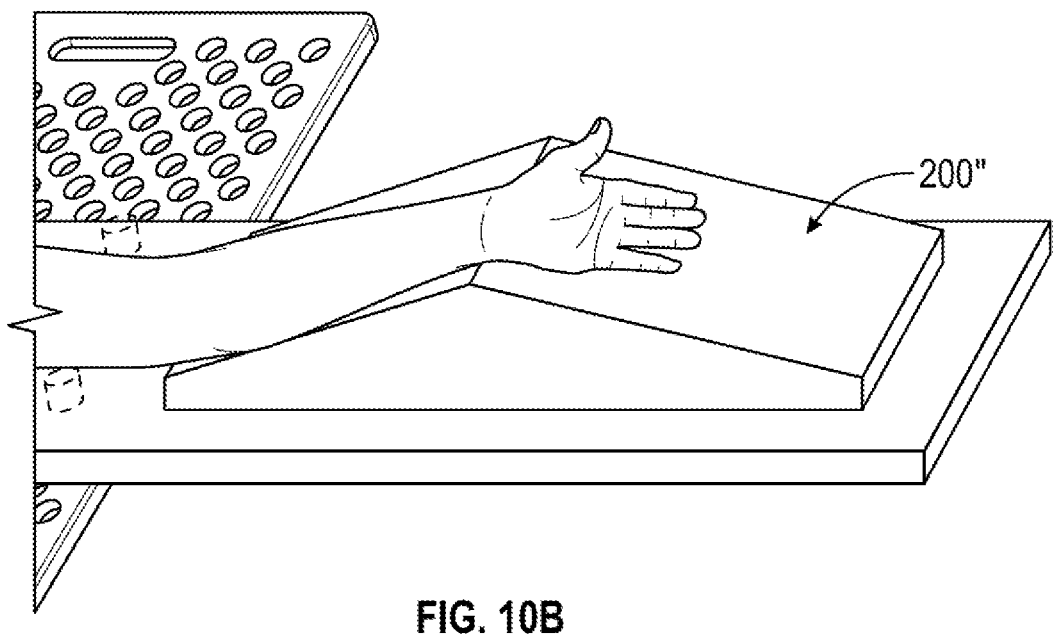

In another exemplary embodiment, as shown in FIG. 8, the MPPS 10 may include additional pegboards for supporting various other body portions. For example, in FIG. 8 an arm pegboard 100 is shown that can be connected to the second pegboard 30. In FIG. 8, the arm pegboard 100 extends outwardly beyond side edges of the second pegboard 30 and surgical table T, and may support an arm positioning member 200" and a patient's arm for being operated on as shown in FIG. 10B. As shown in FIG. 10A, an arm positioning member 200' that can be connected to the pegboard by pegs can support the patient's arm outwardly.

Figure 9A:
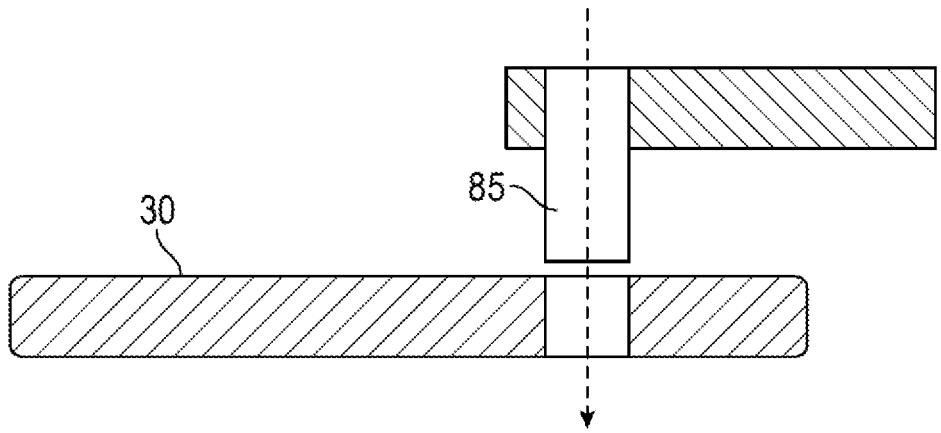
FIG. 9A, FIG. 9B, FIG. 9C show different exemplary ways in which additional pegboards, such as the arm pegboards of FIG. 8, may be connected to the rest of the MPPS.
Figure 9B:
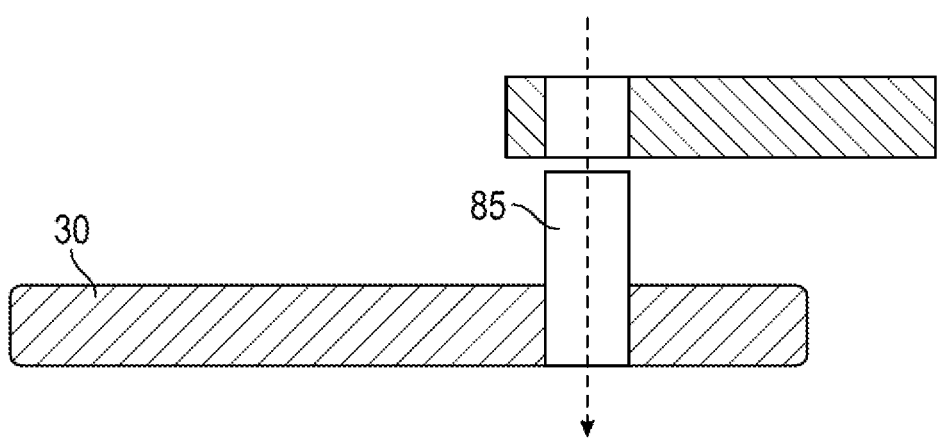
Figure 9C:
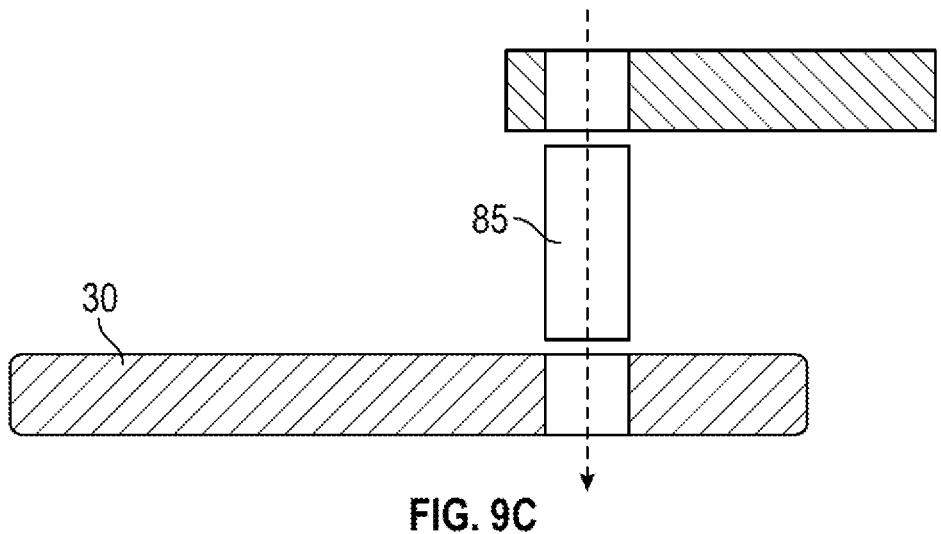

As shown in FIG. 9A, pegs 85 may be permanently affixed to the arm (or other additional) pegboard to be received in the pegboard holes 35 of the first pegboard 25 or second pegboard 30. As shown in FIG. 9B, pegs 85 may be permanently affixed to the first pegboard 25 or second pegboard 30 to be received in the pegboard holes 35 of the additional pegboard 100. Yet further, as shown in FIG. 9C, the pegs 85 may be separate elements that are received in the pegboard holes 35 of the first pegboard 25 or second pegboard 30 and pegboard holes 35 in the additional pegboard 100.

As shown in FIG. 10A, when a first exemplary arm pegboard with a first exemplary positioning member 200' does not extend beyond the edges of the second pegboard 30 and the surgical table T, a patient's arm may be supported/stabilized in a first operating position while surgery on the supported arm or opposite shoulder is performed. As shown in FIG. 10B, when a second exemplary arm pegboard with a second exemplary positioning member 200" extends beyond the edges of the second pegboard 30 and the surgical table T, the patient's arm may be supported in a different operating position and/or flexed or relaxed. These multiple positions allow for proper positioning and support on a patient's arm/wrist/hand during surgery thereon. For sake of convenience, as used in the disclosure and claims "arm" shall be construed to be any body portion below the shoulder, including but not limited to, upper arm, elbow, lower arm, wrist, hand, or fingers. Similarly "leg" shall be construed to cover any body portion between the tips of the toes and the hip/pelvis.

Figure 11A:
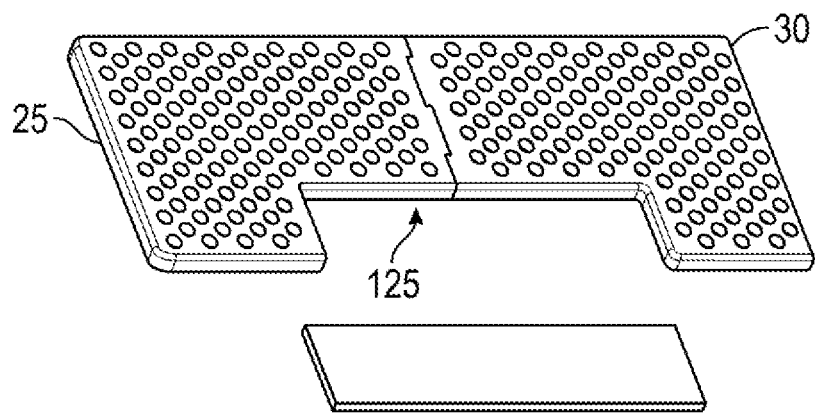
FIG. 11A, FIG. 11B, FIG. 11C show additional exemplary embodiments of the MPPS; in these exemplary embodiments, the MPPS includes an x-ray facilitating cut-out.
Figure 11B:
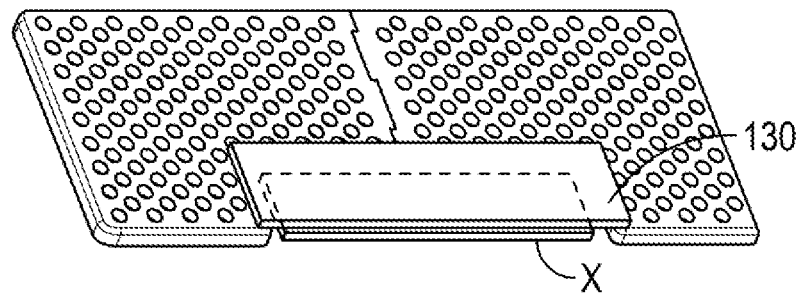
Figure 11C:
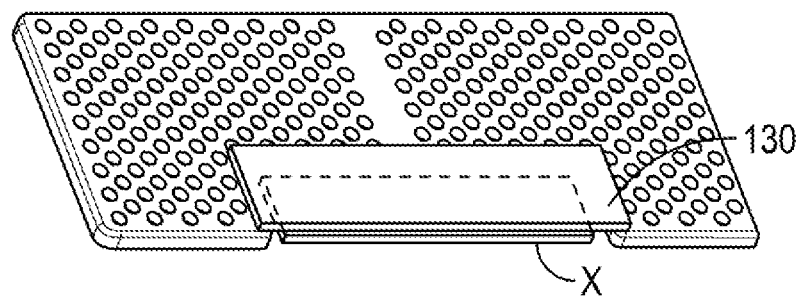

Another feature that the MPPS may include is schematically shown in FIGS. 11A, 11B, 11C, wherein at least one of the pegboards 25, 30 has a cut-out 125 therein. This cutout allows an x-ray film (or cassette) X to be inserted into the area of the cut-out 125 for taking an unobstructed x-ray of the patient, i.e., without the blocking of the dense solid portions of the pegboard. As shown in FIG. 11B, a thin radiolucent cover 130 may be positioned over the cut-out 125 for receiving the x-ray film X thereunder while supporting the patient's body so there is no contact between the x-ray film X and the patient's skin. In FIG. 11C, the single pegboard of FIG. 1B is provided with cutout 125.

Figure 12A:
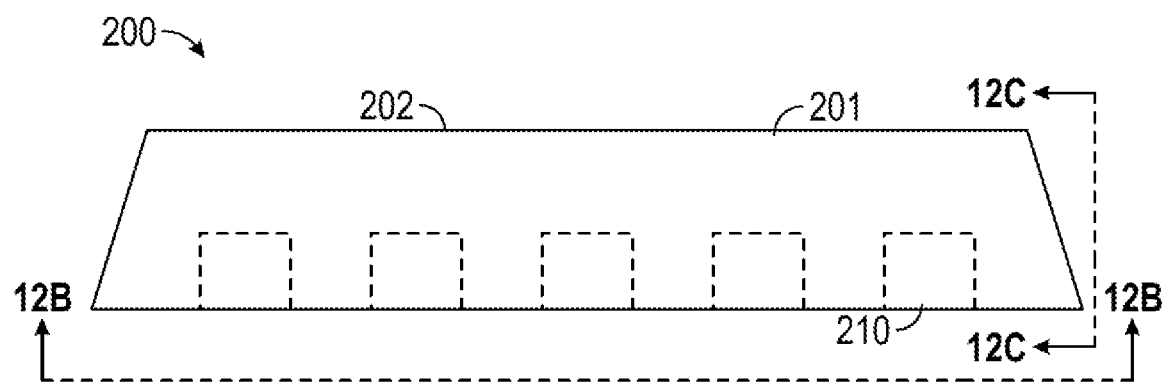
FIG. 12A, FIG. 12B, and FIG. 12C show another exemplary embodiment of the MPPS; in this exemplary embodiment, a generic positioning member for retaining a portion of the patient's body that is to be operated on in a desired surgical position using pegs as a supporting/holding mechanism is included.
Figure 12B:
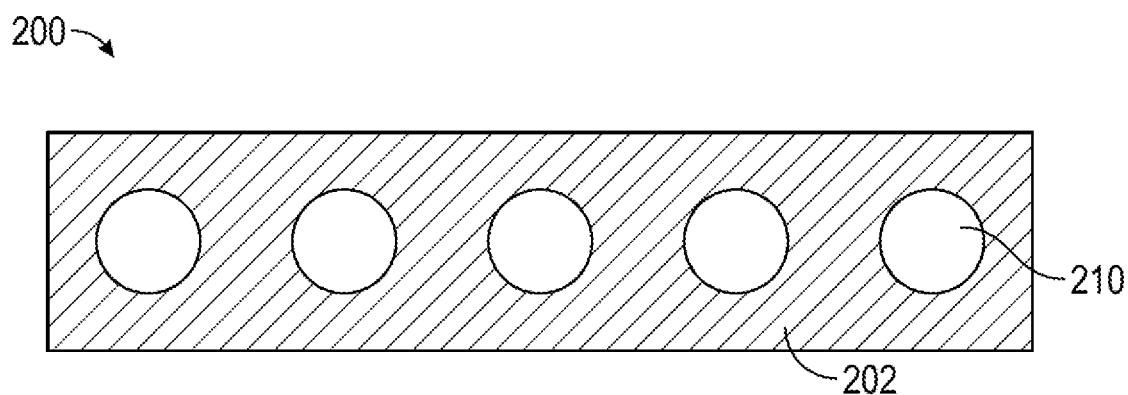
Figure 12C:
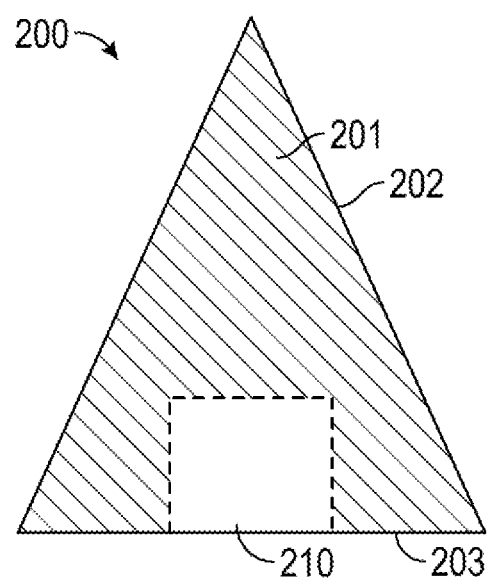

Another feature that the MPPS may include is shown in FIG. 12A, FIG. 12B, FIG. 12C. This feature includes a generic patient positioning member 200 used to cover at least two pegs 85 being used to retain the portion of the patient's upper body that is to be operated on in a desired surgical position. Conventionally, in prior art methods, one peg, in combination with tape, is used to position the pad and retain it in its proper position. As shown in FIG. 12A, FIG. 12B, FIG. 12C the positioning member 200 comprises a positioning pad 201 (also known in the art as cushion or pillow). The positioning pad 201 has an upper portion 202 and a lower portion 203; the upper portion 202 for contacting a portion of the patient's body; and the lower portion 203 having a plurality of blind holes 210 for receiving pegs 85.

Figure 13:
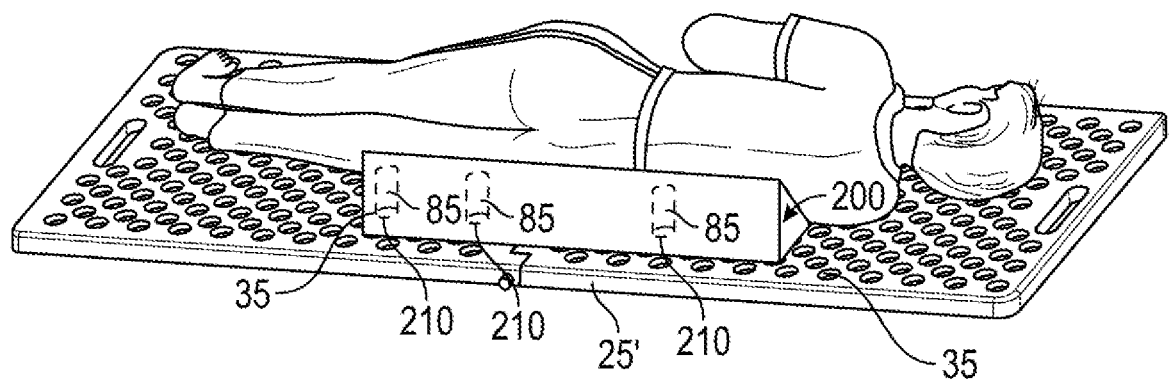
FIG. 13 shows the exemplary generic positioning member of FIGS. 12A, 12B, and 12C, in use to position a patient's body in a laterally upright configuration.
Figure 14A:
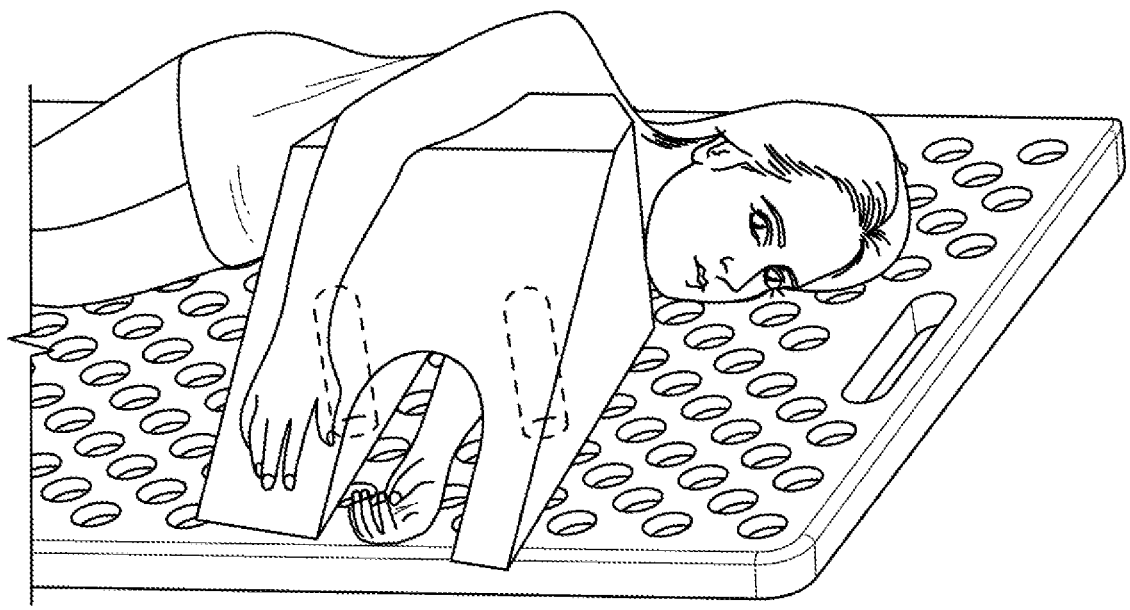
FIG. 14A-14C, show other exemplary embodiments of an MPPS, these exemplary embodiments including various positioning members for use on surgery on different specific body parts.
Figure 14B:
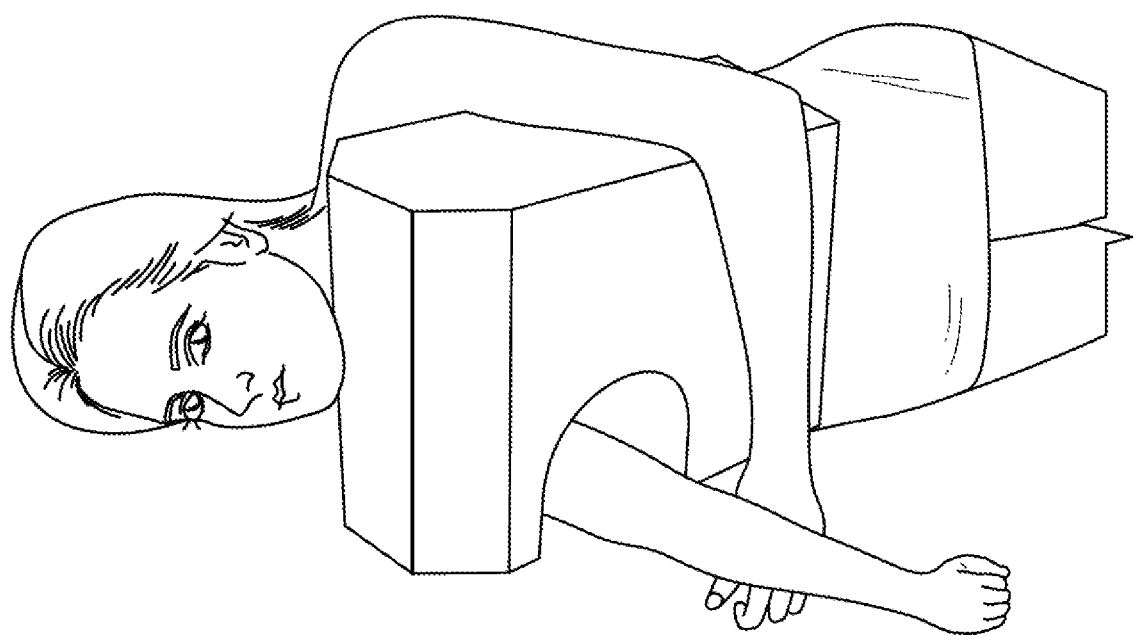
Figure 14C:
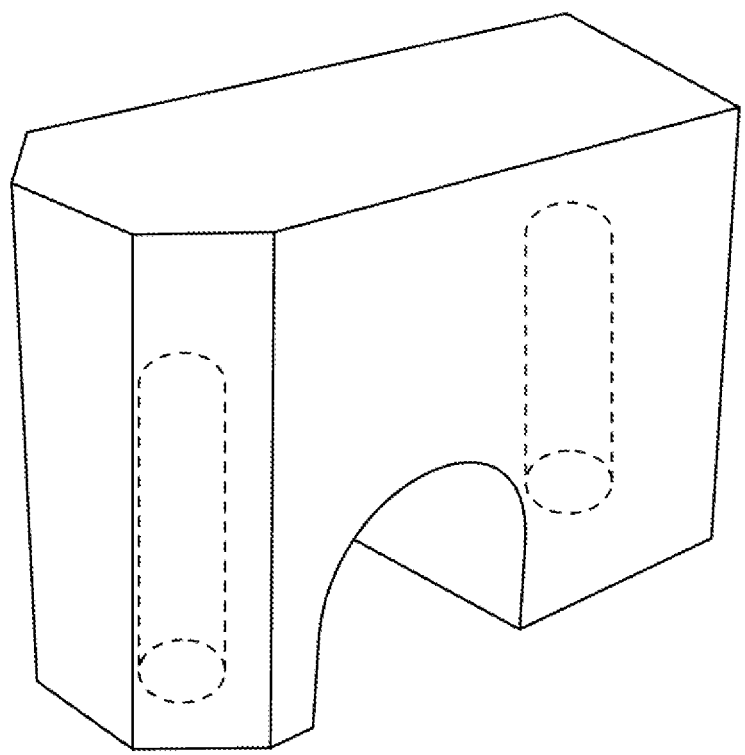

The positioning member 200 can be used either in combination with an MPPS having a first pegboard 25 and second pegboard 30 or with a conventional full-sized pegboard (FIG. 1B). For example, as shown in FIG. 13, the MPPS may include at least one pegboard 25' for positioning on a surgical table and supporting a portion of a patient. Positioning member 200 aligns a portion of a patient's body in a surgical position. The positioning member has a plurality of holes 210 in a lower portion thereof. A plurality of pegs 85 are positioned in pegboard holes 35 at locations where it is desired to position the positioning member 200. The positioning member 200 is then placed over the plurality of pegs 85, by the pegs 85 being received in the holes 210 in the lower portion of the positioning member 200. Conventionally, in prior art methods, positioning pads are fixed with tape to the table or pegboard to retain it in its proper position, or pads are wrapped around a single peg when the patient is fixed in a lateral position. FIG. 14A, FIG. 14B, and FIG. 14C show other exemplary configurations for positioning member 200, useful with different and specific surgical procedures on various body parts.

Figure 15A:
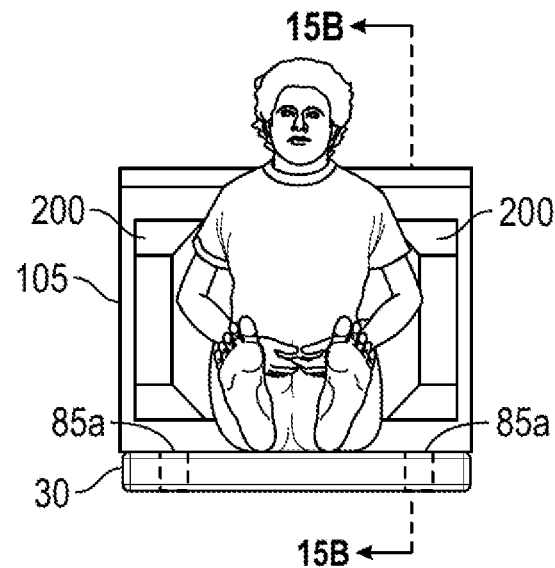
FIG. 15A and FIG. 15B show an exemplary embodiment of an MPPS for facilitating surgery on a patient's neck and/or shoulder area.
Figure 15B:
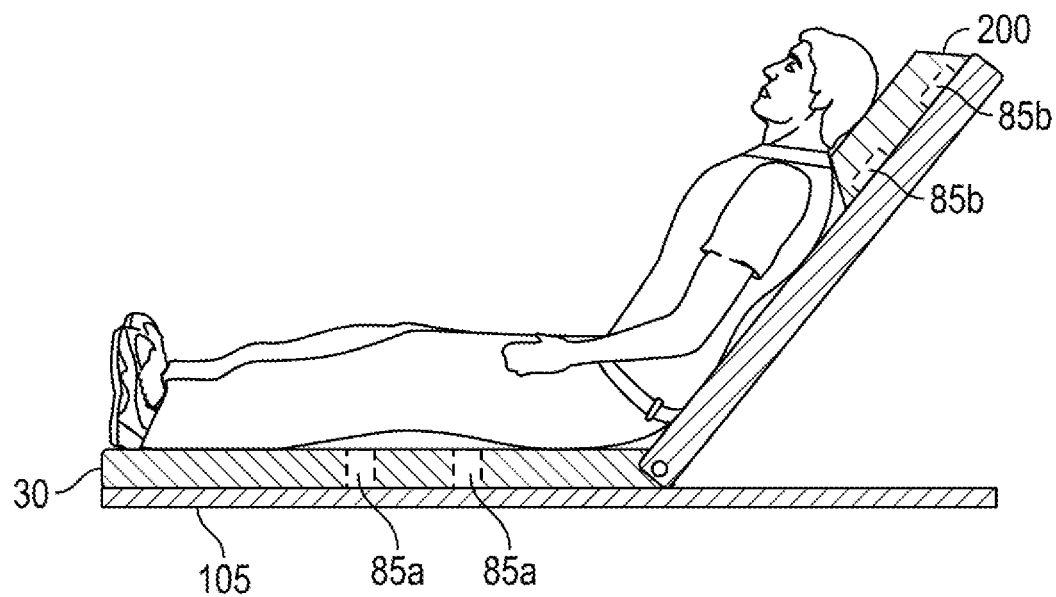

FIG. 15A and FIG. 15B show an exemplary embodiment of an MPPS for facilitating surgery on a patient's neck and/or shoulder areas. In this exemplary embodiment, a first set of pegs 85a are used to attach another (e.g., neck) pegboard 105 to the upper portion/free end of the second pegboard 30. A second set of pegs 85b protrude from the neck pegboard 105 on each side of the patient's neck. Finally, positioning members 200 are placed over pegs 85b, as previously described. This configuration allows for a neck/shoulder positioning that is comfortable to both the doctor and patient.

Figure 16A:
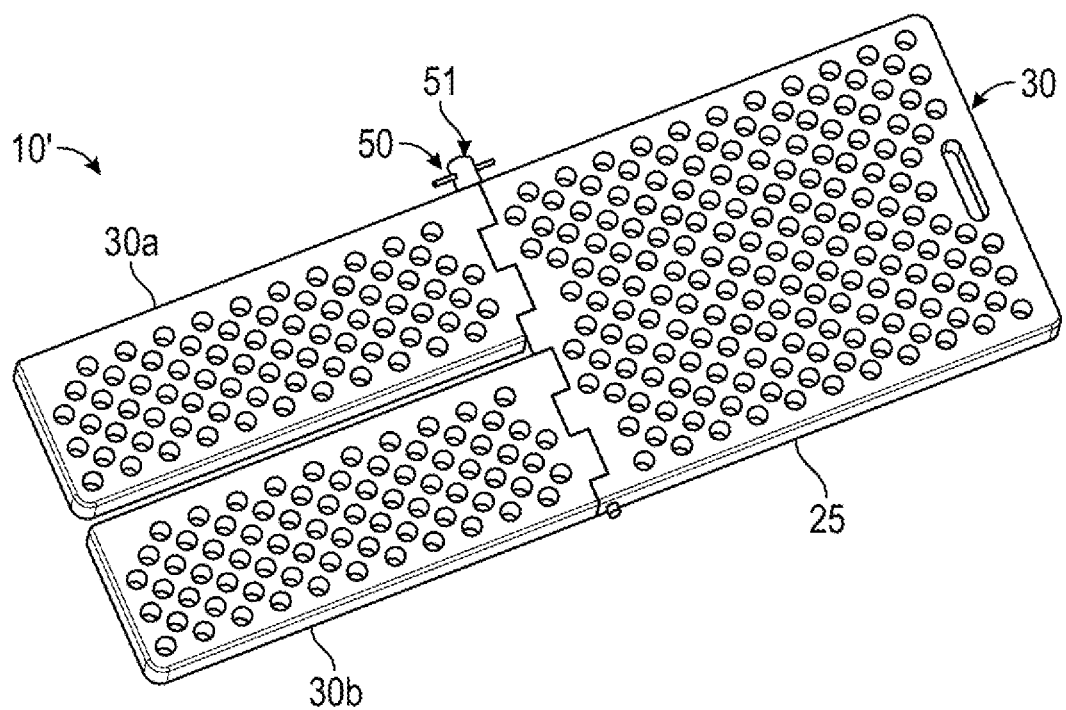
FIG. 16A and FIG. 16B show additional exemplary embodiment of an MPPS.
Figure 16B:
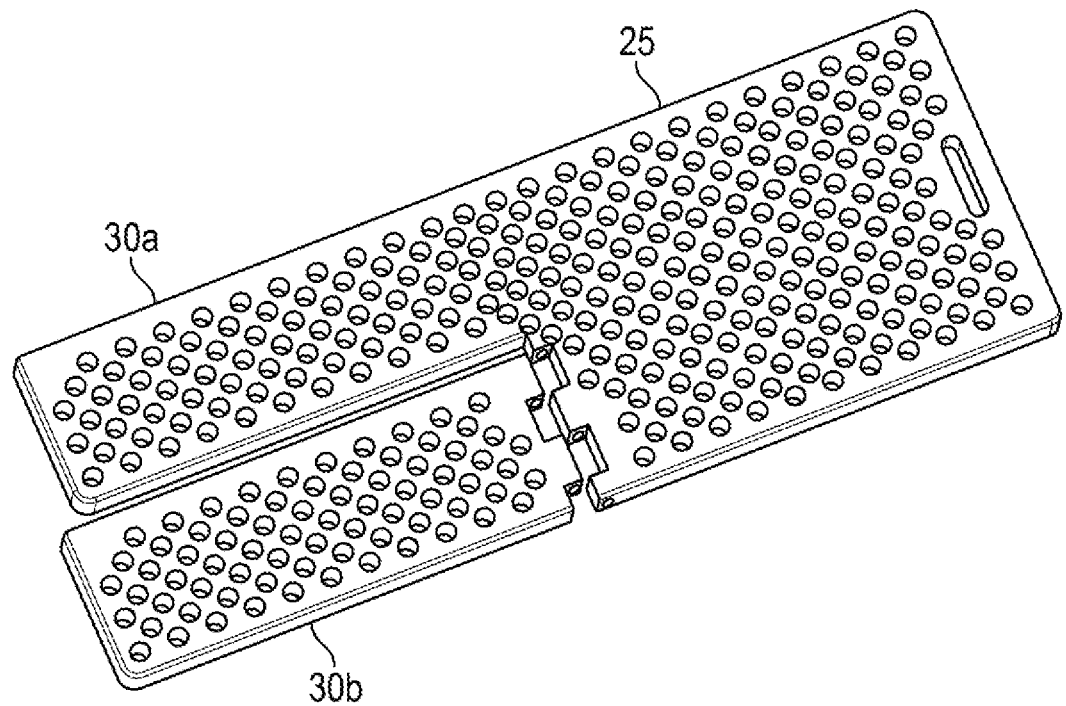

FIG. 16A shows another exemplary embodiment of an MPPS. In FIG. 16A, MPPS 10' is similar to the MPPS 10 of FIG. 1. The difference between MPPS 10' and MPPS 10 is that MPPS 10' has one of pegboards 25, 30, divided into two, separately rotatable pegboard parts, e.g., 30a, 30b. Furthermore, in FIG. 16B, pegboard part 30b is not hinged to the rest of the pegboard 25. In FIG. 16B, pegboard parts 30b may be clamped to the surgical table T in manners previously described. Typically, pegboard parts 30a, 30b will each have substantially the same width, and their combined width will be substantially equal to the width of the other pegboard, e.g., 25.

Figure 17:
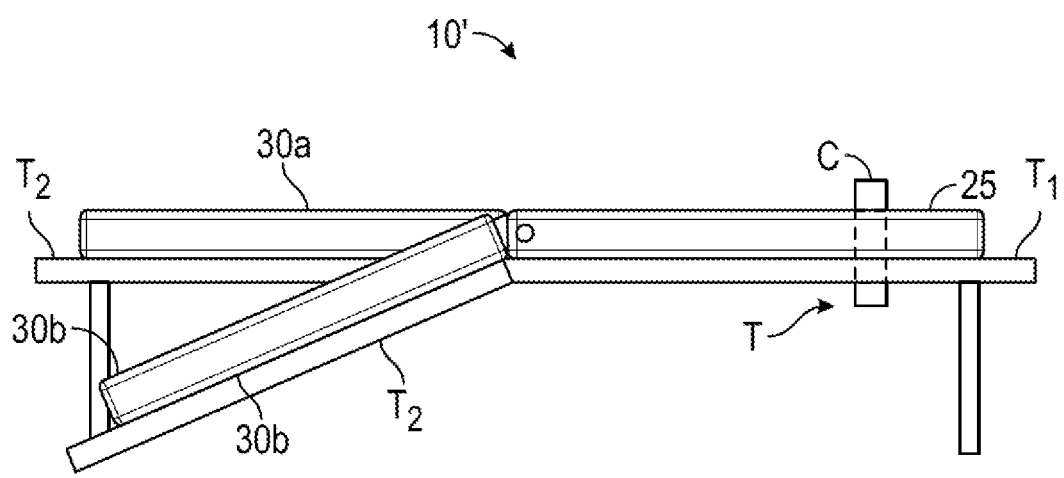
FIG. 17 shows the exemplary embodiment of the MPPS of FIG. 16 in a configuration for surgery on a portion of a patient's lower body and positioned on a surgical table, similar to FIG. 3A, FIG. 3B, and FIG. 3C.

FIG. 17 shows the exemplary embodiment of the MPPS of FIG. 16A in a configuration for surgery on a portion of a patient's lower body and positioned on a surgical table, similar to FIG. 3A, FIG. 3B, and FIG. 3C. In FIG. 17, MPPS 10' is supported on (by) a surgical table T (schematically shown). First pegboard 25 may be clamped to a first, typically fixed-position part T1 of the surgical table T by a clamp C. The second pegboard portions 30a, 30b, are supported in a raised or lowered position by a rotatable portion T2 of the surgical table T and may or may not be clamped to rotatable portion T2.

Figure 18A:
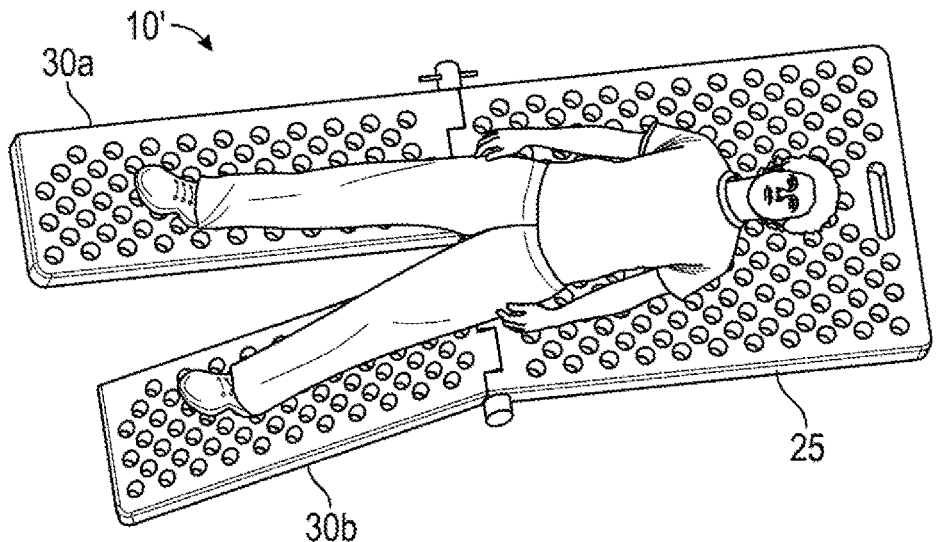
FIG. 18A, FIG. 18B, FIG. 18C, FIG. 18D, FIG. 18E show the exemplary embodiment of the MPPS of FIG. 16 in positions for conducting surgery on one of a patient's legs (FIG. 18A), a patient's knee (FIG. 18B), and/or both of a patient's legs (FIG. 18C).
Figure 18B:
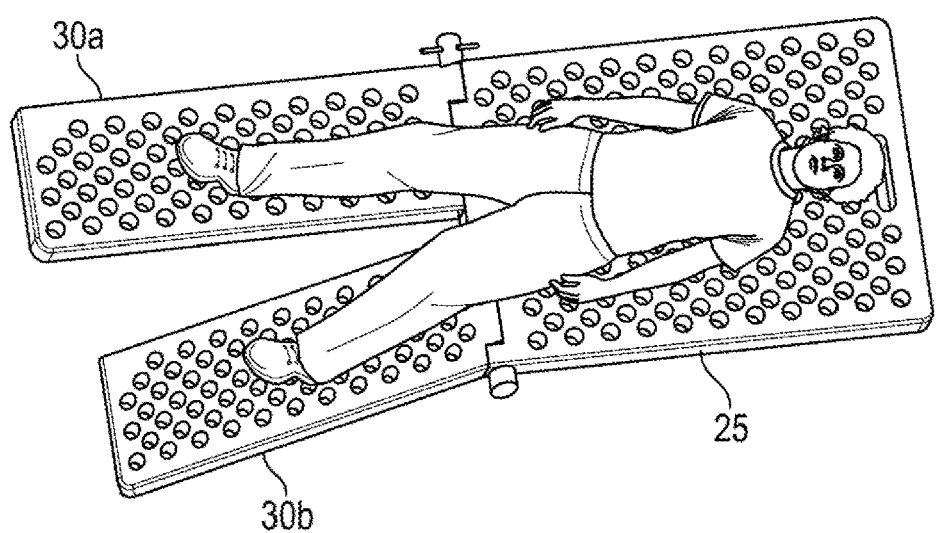
Figure 18C:
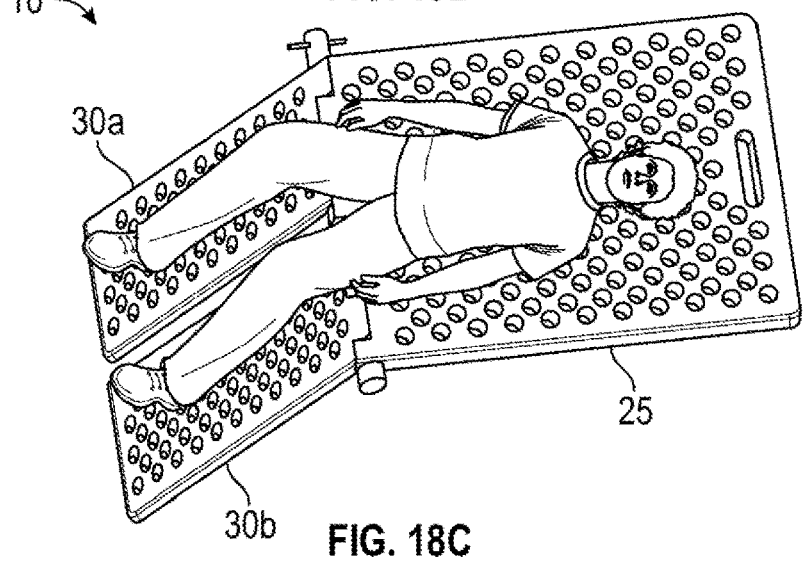
Figure 19A:
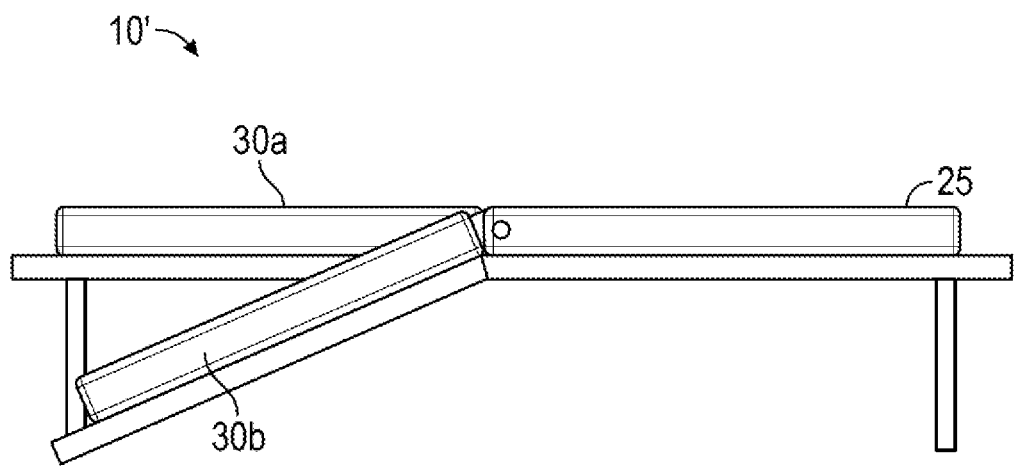
FIG. 19A, FIG. 19B, and FIG. 19C, show the exemplary embodiments of FIGS. 18A, 18B, and 18C, respectively in side views.
Figure 19B:
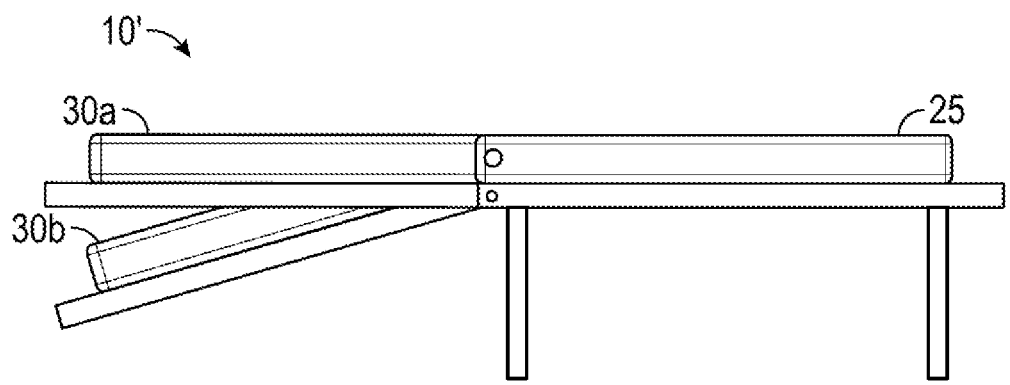
Figure 19C:
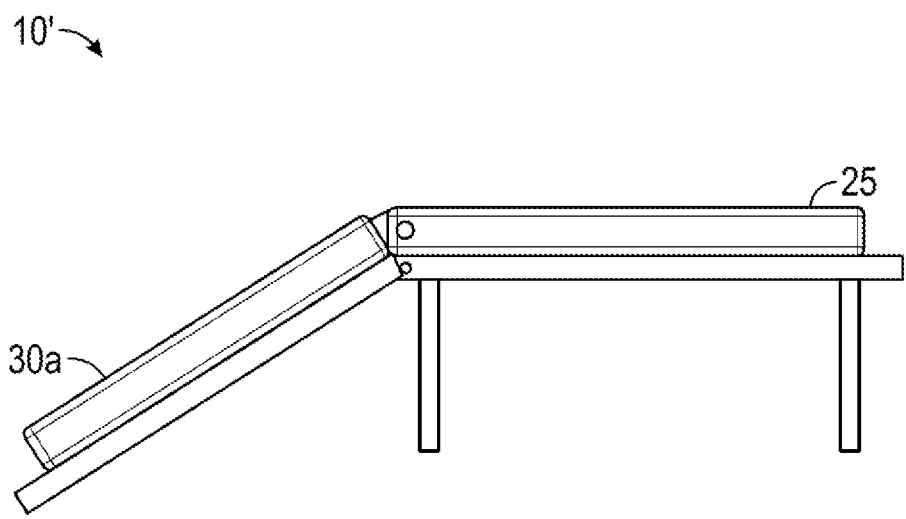

FIG. 18A, FIG. 18B, FIG. 18C each schematically show the exemplary embodiment of the MPPS 10' of FIG. 16 in positions for conducting surgery on one of a patient's legs (FIG. 18A), a patient's knee (FIG. 18B), and/or both of a patient's legs (FIG. 18C). Note that this functionality is useful because often, when a leg is being operated on, it may be angled in an up or down positioning to check rotation, provide visibility to all portions of the joint, and extend or relax muscles and ligaments. For clarity, FIG. 19A, FIG. 19B, and FIG. 19C, show the exemplary embodiments of FIGS. 18A, 18B, and 18C, respectively in side view.

In FIG. 18A, the patient's hip is generally aligned with the pivot axis between the first pegboard and the second pegboard. Therefore, pivoting of the pegboards cause either tensioning or extension (extend or relax) of the hip muscles. In FIG. 18B, the patient's knee is generally aligned with the pivot axis between the first pegboard and the second pegboard. Therefore, pivoting of the pegboards cause either tensioning or extension (extend or relax) of the knee muscles. To further accurately position a portion of a leg, such as a knee or hip during surgery, a leg positioner 300 may be used.

Figure 18D:
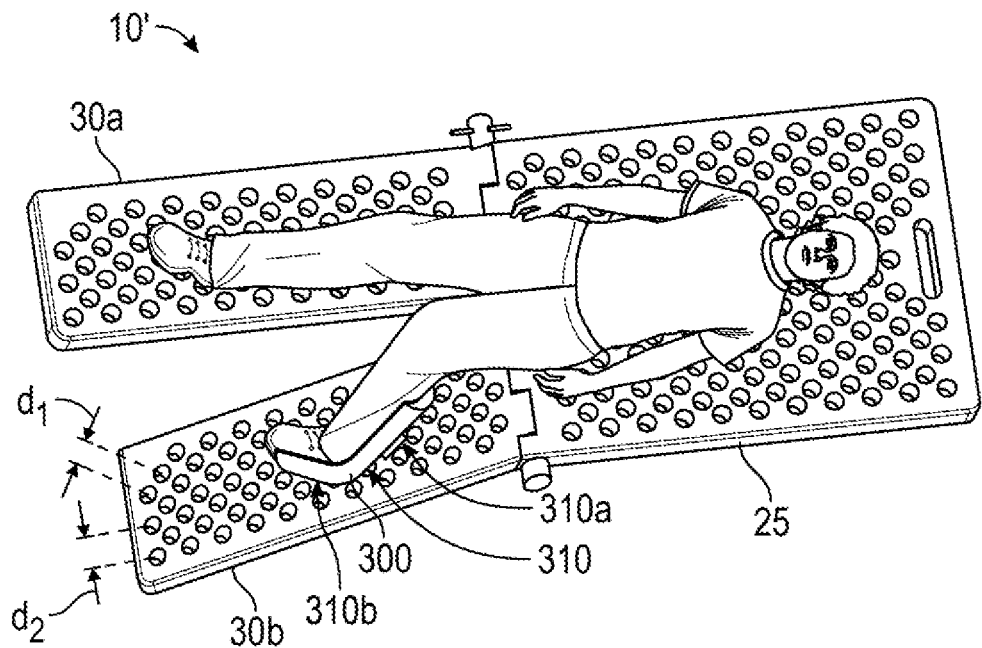
Figure 18E:
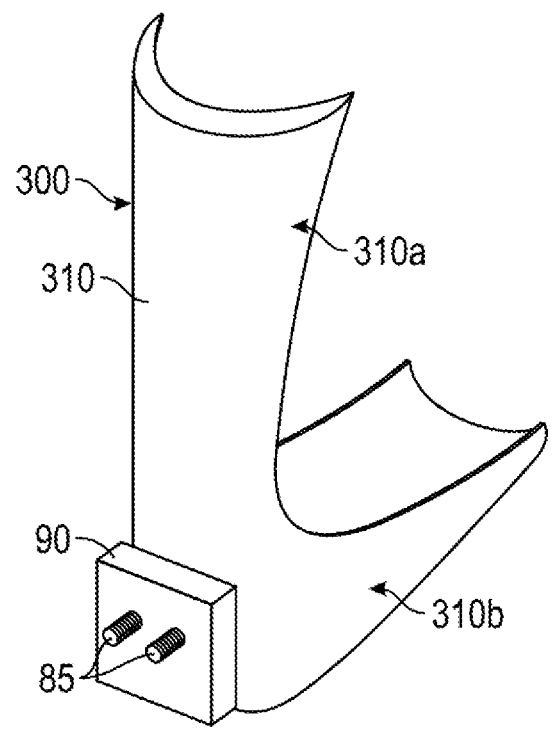

A first exemplary embodiment of a leg positioner is shown in FIG. 18D and FIG. 18E. In this exemplary embodiment, peg holes located along a line oblique to the lateral or longitudinal axes of the pegboard may have a center to center distance of d1. Peg holes located along the lateral or longitudinal axis of the peg board may have center to center distances of d2. Typically, d2>d1. Leg positioner 300 includes a boot 310 having a foot receiving portion 310b for receiving the foot and leg receiving portion 310a for receiving the lower portion of the leg whose knee or hip is being operated on. Pegs 85 are attached to the boot 310 so that the boot 310 can be fixed to pegboard 30b in a desired position that provides the desired flexion/extension and/or distraction/compression on the knee or hip, when pegboard 30b is adjusted. While not necessary, a mounting block 90 may also be provided to ease the shearing forces on pegs 85. While not shown, it is possible that a surgical boot having a peg directly attached thereto can be used to attach the foot to the pegboard to assist in flexing/extending and/or distracting/compressing the knee or hip.

In FIG. 18E, mounting block 90 and its associated pegs are attached to leg receiving portion 310a. In FIG. 18E, there are typically just one set of pegs 85 protruding in a direction opposite to the foot receiving portion.

Figure 18F:
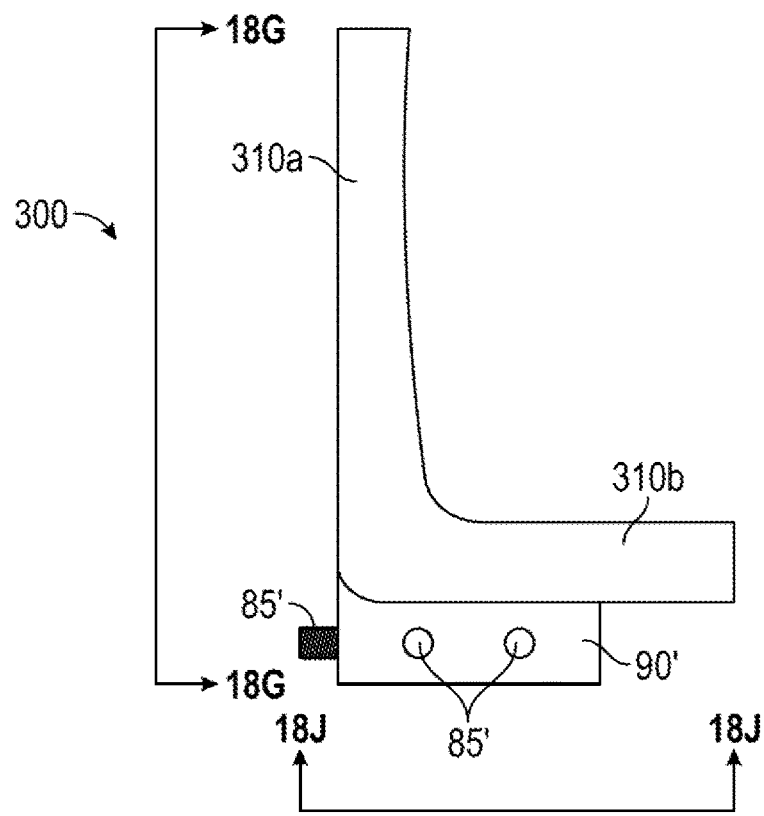
FIG. 18F and FIG. 18G show a different structure of a leg positioner that can be used to achieve one or more of various anatomical positionings.

In FIG. 18F, block 90 and its associated pegs are attached to foot receiving portion 310b. In FIG. 18F, there are typically multiple sets of pegs 85' protruding at least in directions both perpendicular to the foot receiving portion and parallel to the foot receiving portion (perpendicular to the leg receiving portion).

Figure 18G:
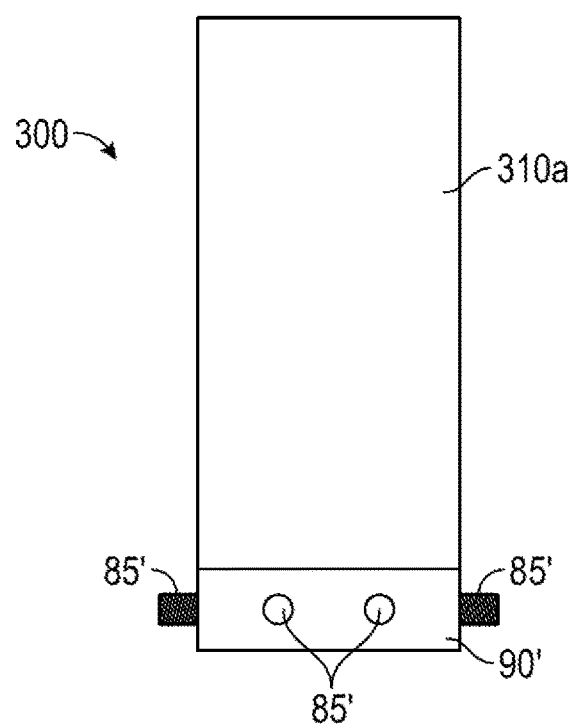
Figure 18H:
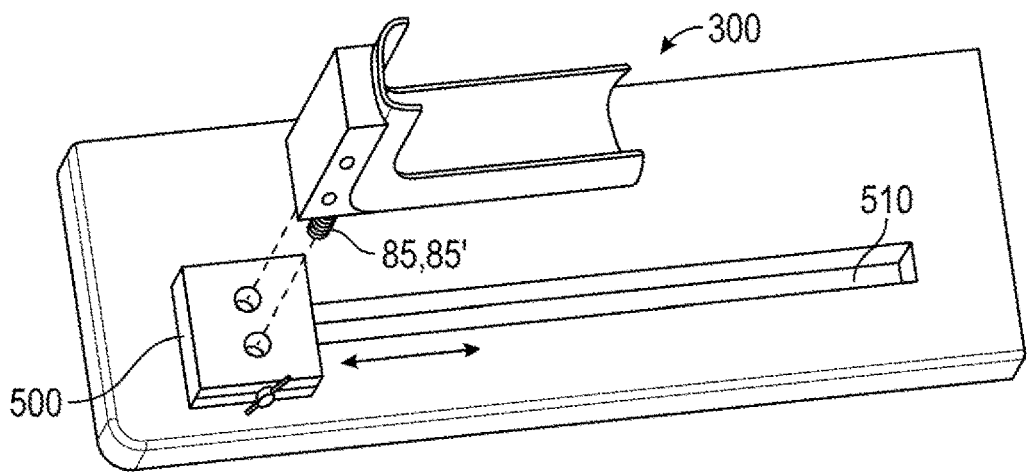
FIG. 18H shows yet another exemplary embodiment for adjusting the amount of flexion/extension and/or distraction/compression of at least a portion of the leg based upon the position of the leg positioner relative to the end of a pegboard.
Figure 18I:
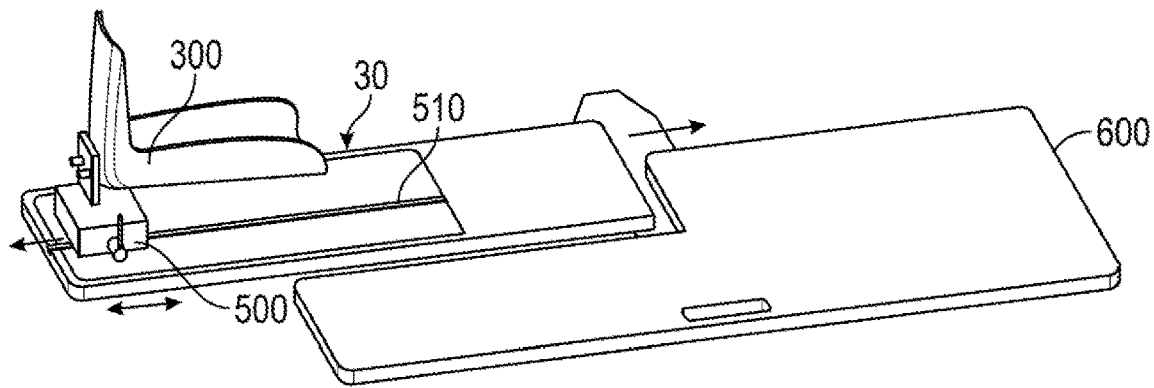
FIG. 18I shows an alternative exemplary embodiment of FIG. 18H.
Figure 18J:
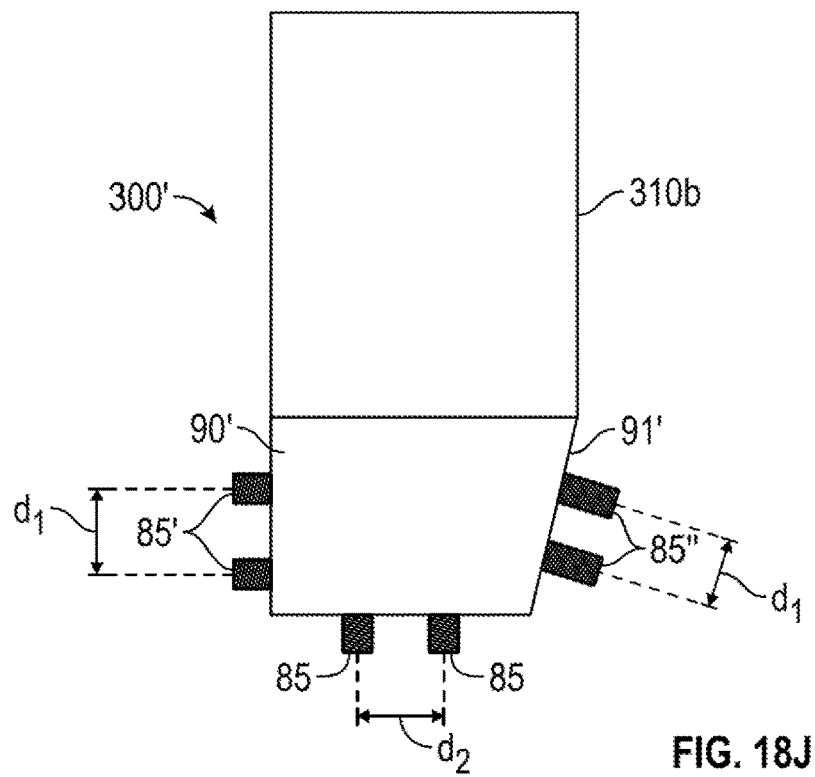
FIG. 18J shows an alternative embodiment of a leg positioner that allows for adjusting the amount of axial rotation of a leg/hip/knee during an orthopedic surgery.
Figure 18K:
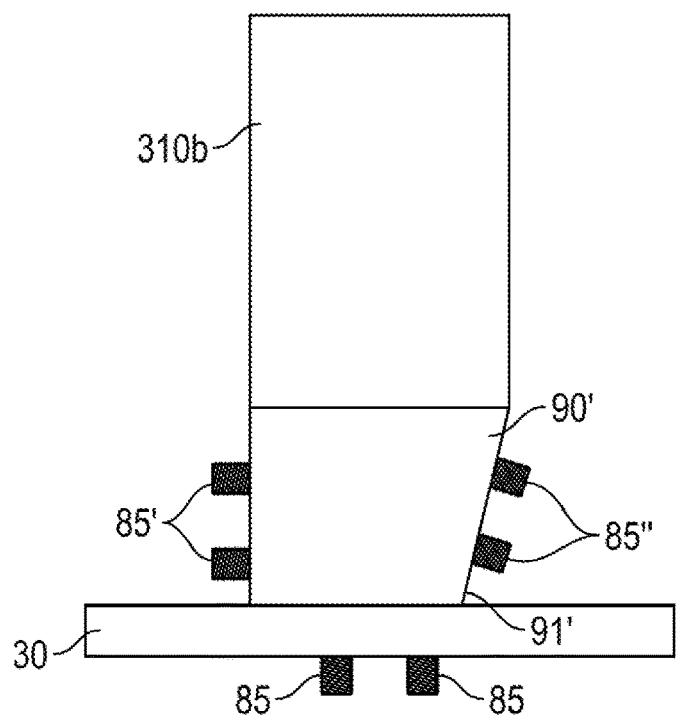
FIG. 18K and FIG. 18L and FIG. 18M show how the axial rotation of the leg can be varied using the alternative leg positioner of FIG. 18J.
Figure 18L:
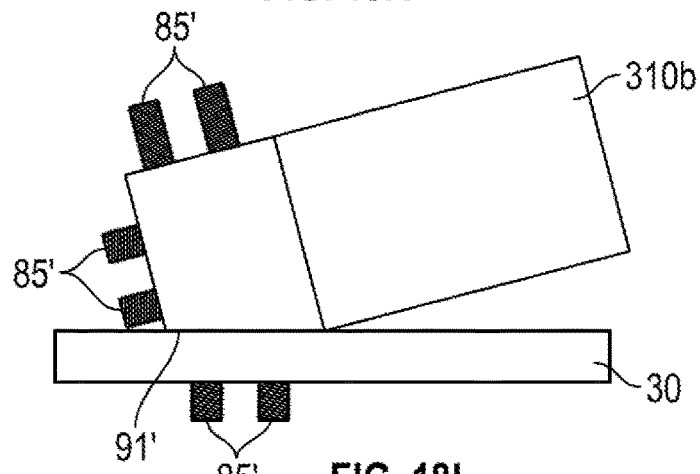

These two different ways in which pegs 85 are attached to boot 310 result in different ways in which boot 310 may be mounted to the pegboard (see FIGS. 18K, 18L, and accompanying description.

FIG. 18F and FIG. 18G show a different structure of a leg positioner 300' and a mounting structure that can be used to achieve one or more of the various anatomical positionings described above.

In FIG. 18F and FIG. 18G, as with FIG. 18E, the amount of flexion/extension can be adjusted based upon the position of the leg positioner relative to the end of the pegboard. The further away from the end of pegboard that the pegs of the leg positioner are inserted into the pegboard, the greater the flexion/extension and/or distraction/compression of the knee or hip.

FIGS. 18H and 18I show other exemplary embodiments for adjusting the amount of flexion/extension based upon the position of the leg positioner relative to the end of the pegboard.

In FIG. 18H, leg positioner 300 is mounted to a slidable block 500, which forms part of the mounting structure and is slidably mounted to a track 510 in the pegboard (the area in which the track is mounted need not have pegboard holes).

Accordingly, in FIG. 18H, the position of 300 can be adjusted by varying the position relative to the end of pegboard at which slidable block 500 is locked or clamped. The further away from the end of pegboard that slidable block 500 is locked or clamped, the more flexion/extension of the knee and hip. The leg positioner 300 can be fixed to slidable block 500 by pegs (FIG. 18H) or directly fixed to slidable block 500 (FIG. 18I). In this exemplary embodiment, board 600 may have pegholes, not have pegholes, or be omitted entirely, wherein the patient's upper body lies directly upon the surgical table.

FIG. 18J shows an alternative embodiment of leg positioner 300' that allows for adjusting the amount of axial rotation of a leg/hip/knee during an orthopedic surgery. In FIG. 18J, the mounting structure includes an optional mounting block 90' located on foot receiving portion 310b, such as it is in FIG. 18F, but different from as shown in FIG. 18E, where mounting block 90 is located on leg receiving portion 310a. Mounting block 90' can have additional pegs 85' and 85" protruding therefrom in a variety of directions. Preferably pegs 85', 85" come in adjacent pairs for stability and rotation prevention. The pair of pegs 85' may have a center-to-center distance of d1. The pair of pegs 85" may also have a center-to-center distance of d1. The pair of pegs 85 may have a center-to-center distance of d2. As previously mentioned, d2>d1. These dimensions are used when corresponding to a peg board, such as exemplified relative to FIG. 18D. If mounting block 90' is square or rectangular, pegs 85' and pegs 85" can protrude from the sides of the mounting block 90'. For increased flexibility of rotation amount, it is preferred that at least three sets of pegs can be provided. Two sets of pegs 85' are to be substantially perpendicular to each other. The third set of pegs 85" are to be oblique relative to the axes of both the sets of pegs 85'. This oblique orientation may be achieved by mounting the pegs on an oblique wall 91' of mounting block 90'.

Figure 18M:
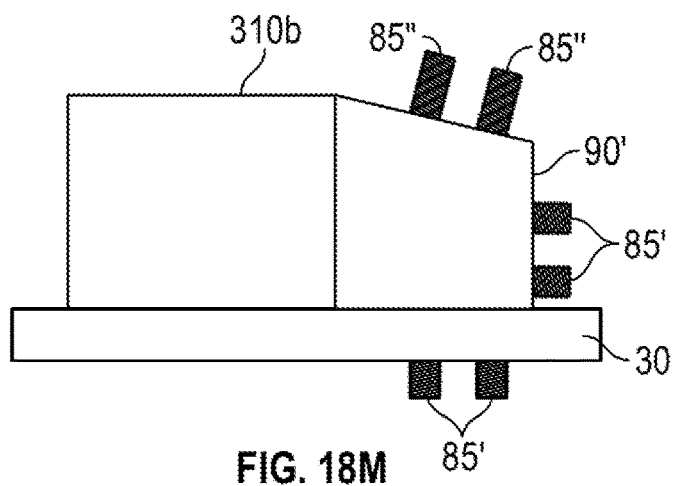

FIG. 18K and FIG. 18L and FIG. 18M show how the axial rotation of the leg can be varied using the alternative leg positioner 300' of FIG. 18J.

In FIG. 18K, by positioning pegs 85' that are parallel to the plane of the foot into the desired pegboard holes, the leg will be positioned with no rotation and the foot substantially perpendicular to the pegboard.

In FIG. 18L, by positioning pegs 85' that are perpendicular to the plane of the foot into the desired pegboard holes, the leg will be positioned with 90 degrees of rotation and the foot substantially parallel to the pegboard.

In FIG. 18M, by positioning pegs 85" that are oblique with the other pegs 85' into the desired pegboard holes, the foot and leg will be positioned with an angle between 0-90 degrees of rotation (e.g. the oblique angle). The oblique wall 91' of mounting block 90' also provides additional stability to the pegs 85".

Figure 18N:
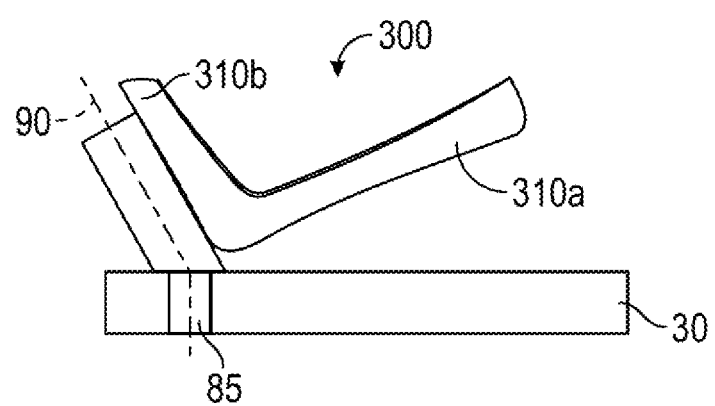
FIG. 18N shows an alternative means by which the position of a leg during surgery can be adjusted.

In FIG. 18N, by having the longitudinal axis of peg 85 be at an oblique angle with block 90', leg positioner 300 will be non-parallel to peg board 30; thereby elevating the knee. Such a positioning can be advantageous to surgery on the leg, etc.

Figure 25A:
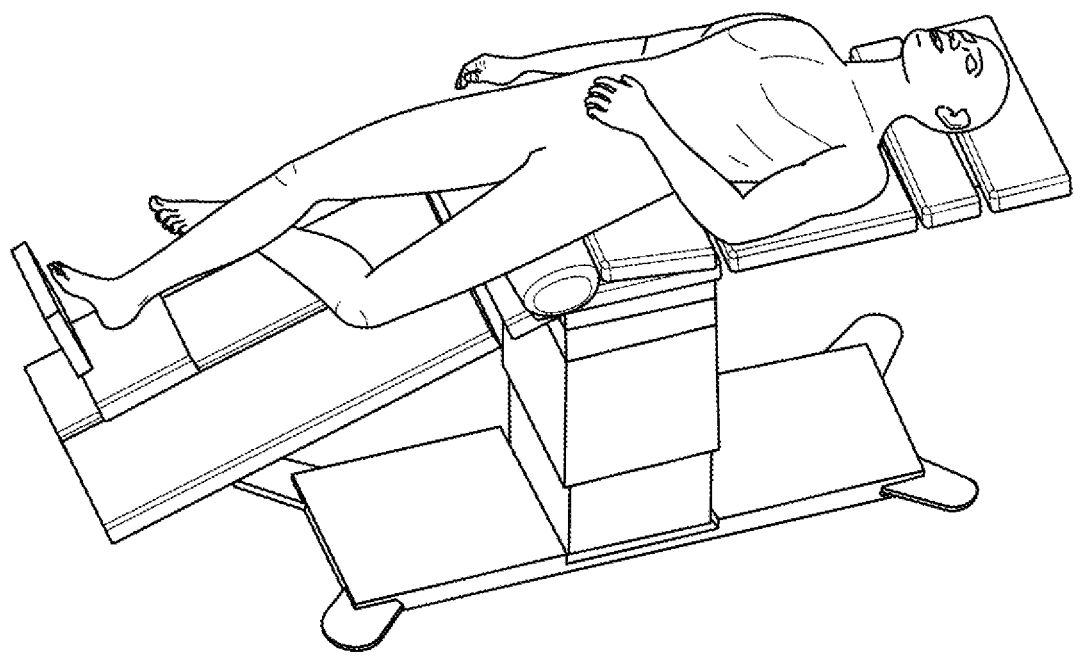
FIG. 25A shows a common leg/knee positioning used during an orthopedic surgery.

FIG. 25A shows a common leg/knee positioning used during an orthopedic surgery. The patient's leg is bent and the lower leg placed under the non-bent leg. This causes flexion/extension and other movements, such as distraction/compression in the bent leg, that make surgery thereon easier.

Figure 25B:
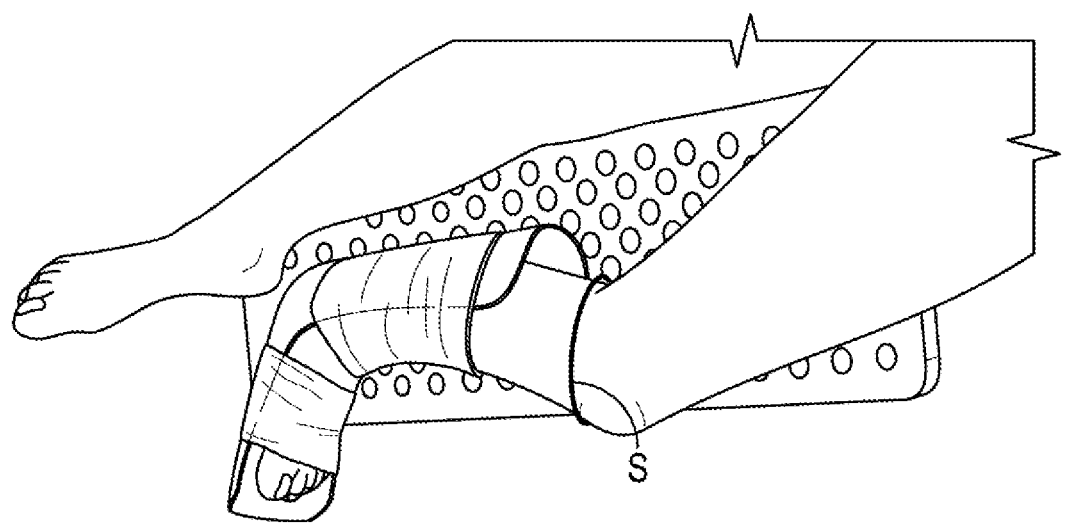
FIG. 25B shows how, by using the exemplary leg positioners described herein, the positioning of FIG. 25A can be achieved and in a more secure manner.

FIG. 25B shows how, by using the exemplary leg positioners described herein, the positioning of FIG. 25A can be achieved and in a more secure manner (by the boot being secure relative to the pegboard/table and the foot being secure relative to the boot). Furthermore, strap S can be used to secure a knee in position, freeing up a nurse that typically is dedicated to holding the knee in place.

The leg positioner 300 and arm positioner 200' (FIG. 10A) can be attached to the pegboards in substantially the same ways.

FIG. 20 shows the exemplary embodiment of the MPPS of FIG. 16 in a configuration for performing surgery on an upper portion of a patient's body. The details of this embodiment are generally the same as those of FIG. 1, except for the fact that second pegboard 25 is formed by two second pegboards 30a, 30b.

FIG. 21A and FIG. 21B are rear views similar to those of FIG. 7A and FIG. 7B, respectively, where different portions of the patient's upper body U2 are supported and different portions of the patient's upper body U1 are unobstructed for surgery thereon. Reference to FIG. 7A and FIG. 7B will generally inform the reader of the features and functionality of FIG. 21A and FIG. 21B.

Figure 22:
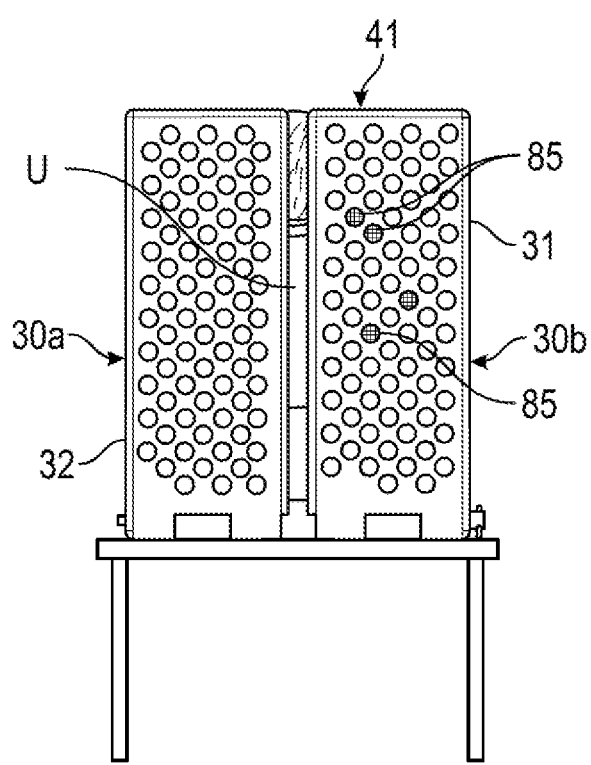
FIG. 22 is a rear view, similar to the rear views of FIG. 21A and FIG. 21B, but showing where the MPPS is configured to support substantially the entire upper body.

FIG. 22 is a rear view, similar to the rear views of FIG. 21A and FIG. 21B, but showing where MPPS 10' is configured to support substantially the entire upper body U. Again, reference to FIG. 7A and FIG. 7B will generally inform the reader of the features and functionality of FIG. 22.

Figure 26:
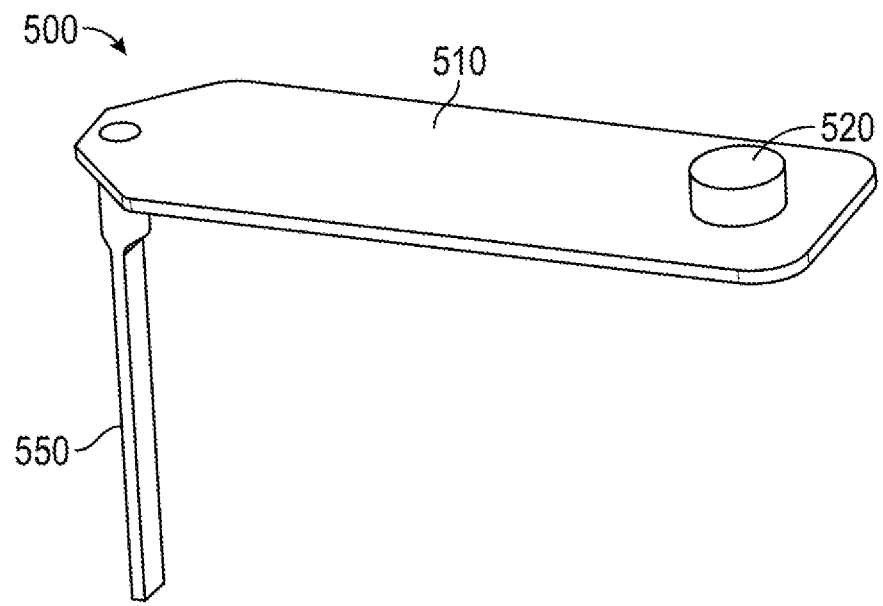
FIG. 26 shows a pivot system that can be used with the adjustable pegboard systems described herein for use in controlling the amount of abduction/adduction.

FIG. 26 shows a mounting structure including a pivot system that can be used with, for example, the legs positioners 300, 300' and adjustable pegboard systems described above for use in controlling the amount of abduction/adduction. The pivot system includes a pivot support 500. Pivot support 500 comprises a main body 510. A pivot peg 520 protrudes in a first direction from a first side and first end of main body 510. A mounting bar 550 protrudes in a second direction, generally opposite from the first direction, from a second side and second end of main body 510. A clamp (not shown) is used in combination with mounting bar 550 to attach pivot support 500 to a surgical table or pegboard. Typically, when in use, the first direction is upwards and the second direction is downwards.

Figure 27:
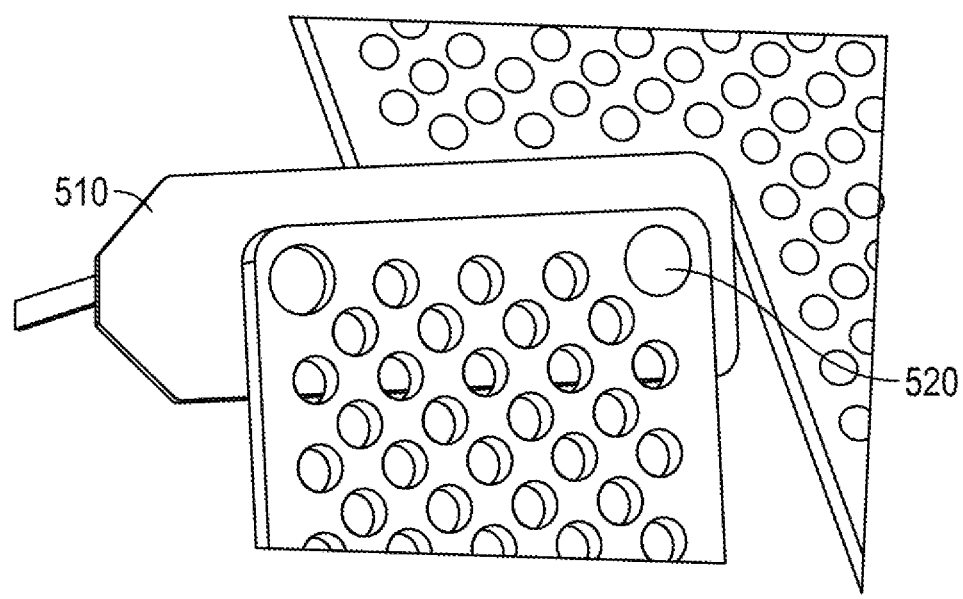
FIG. 27 shows how the pivot system of FIG. 26 is set up.
Figure 29A:
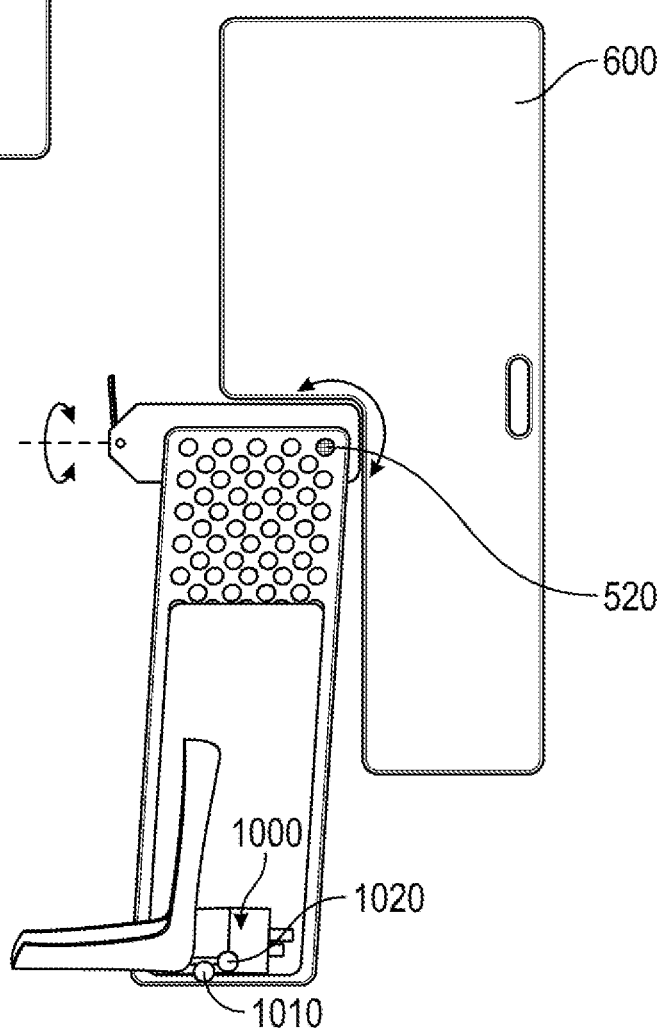
FIGS. 29A and 29B show a second exemplary way of how the pivot system of FIGS. 26, 27 can be used, respectively.
Figure 29B:
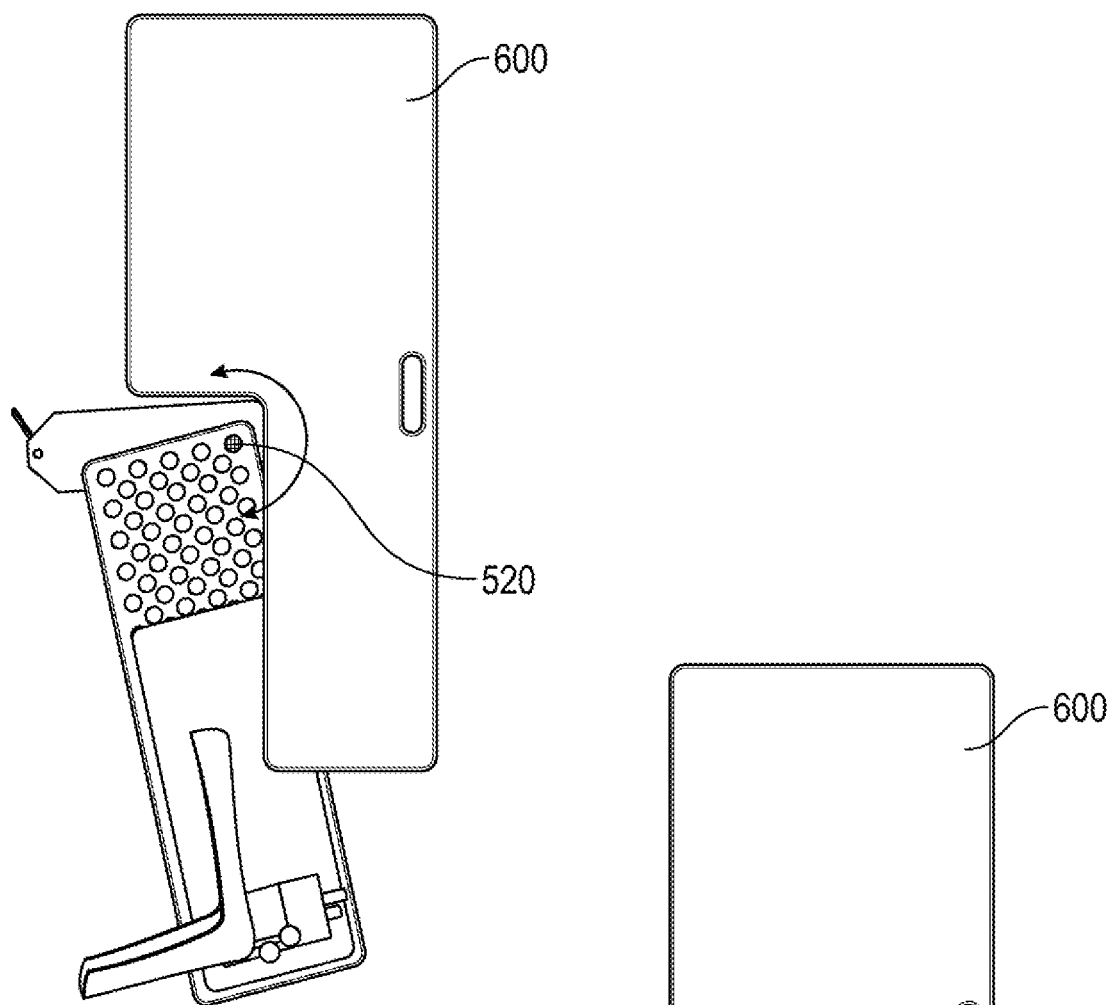
Figure 29C:
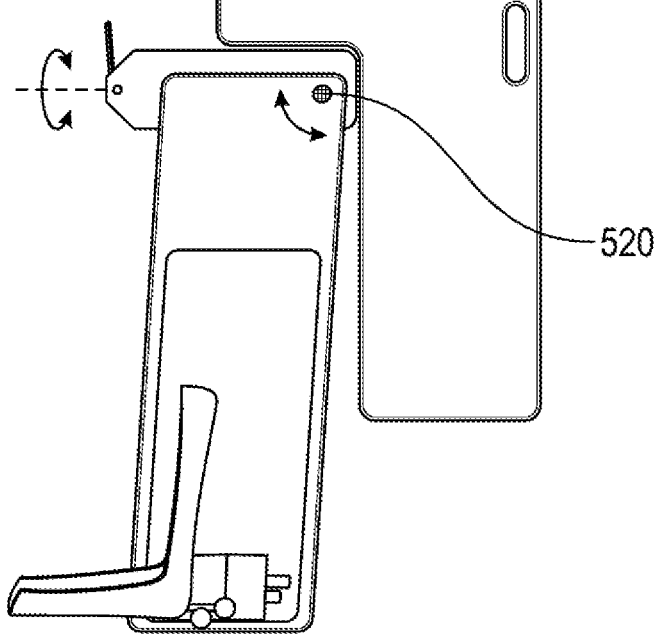
FIG. 29C shows the pivot system of FIGS. 26, 27 in combination with a pivotable board that is not a pegboard.
Figure 30A:
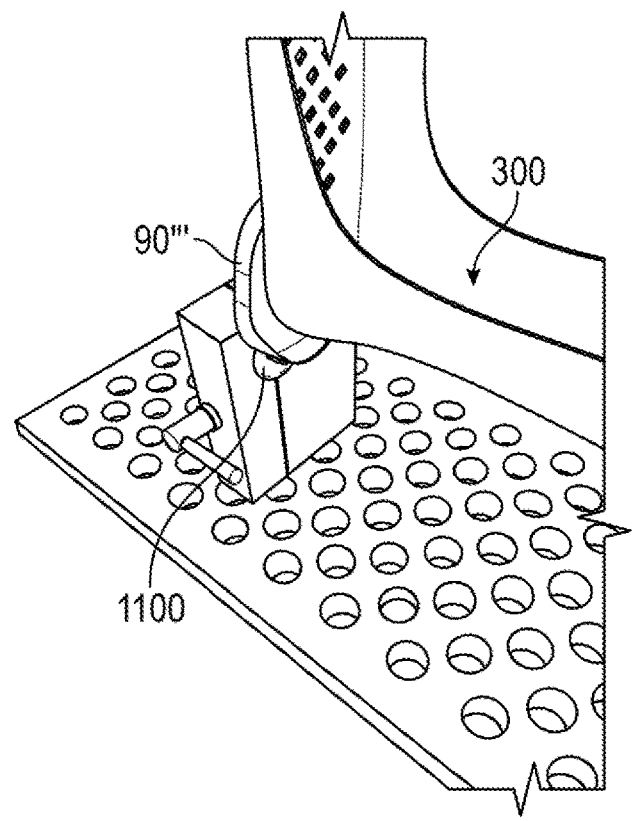
FIGS. 30A, 30B, 30C, and 30D depict an alternative exemplary embodiment for a mounting structure that allows for varying the position or elevation of the knee.
Figure 30B:
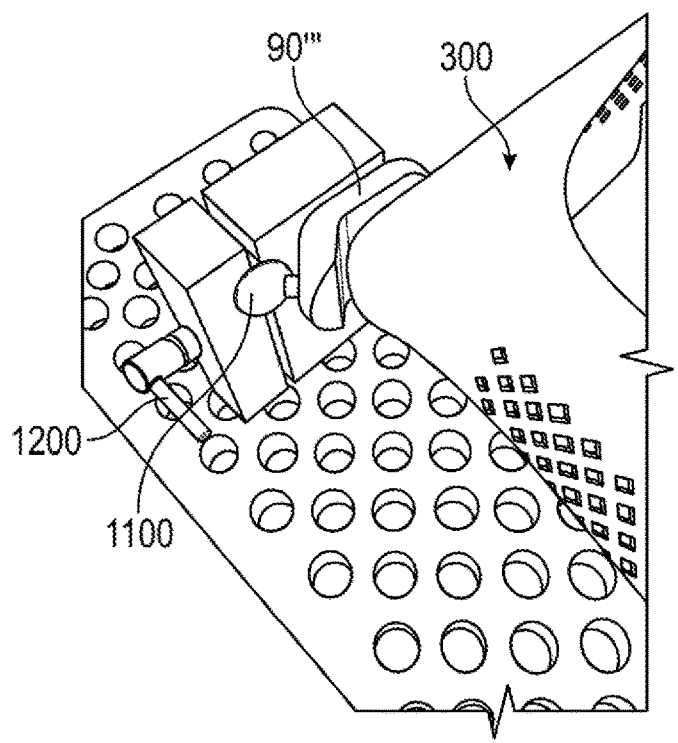
Figure 30C:
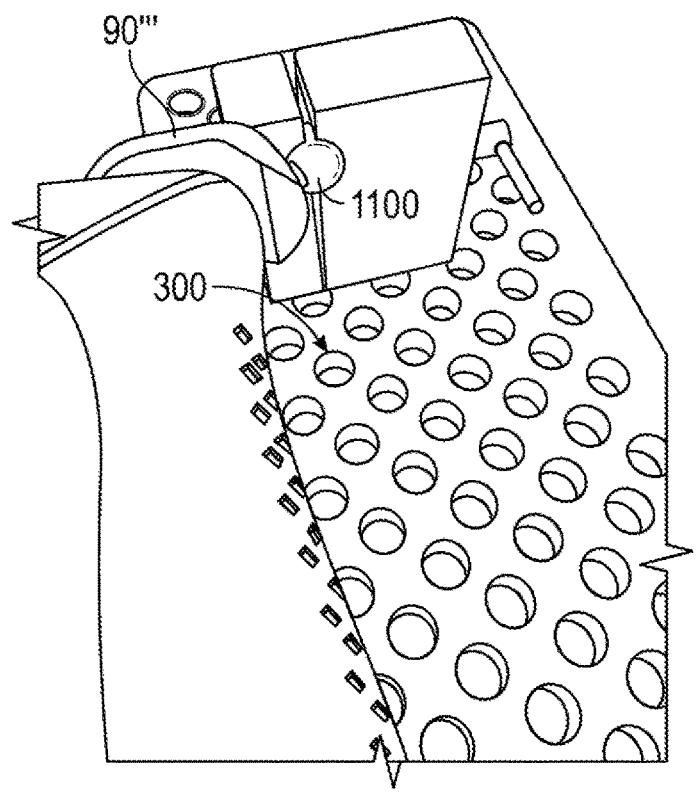
Figure 30D:
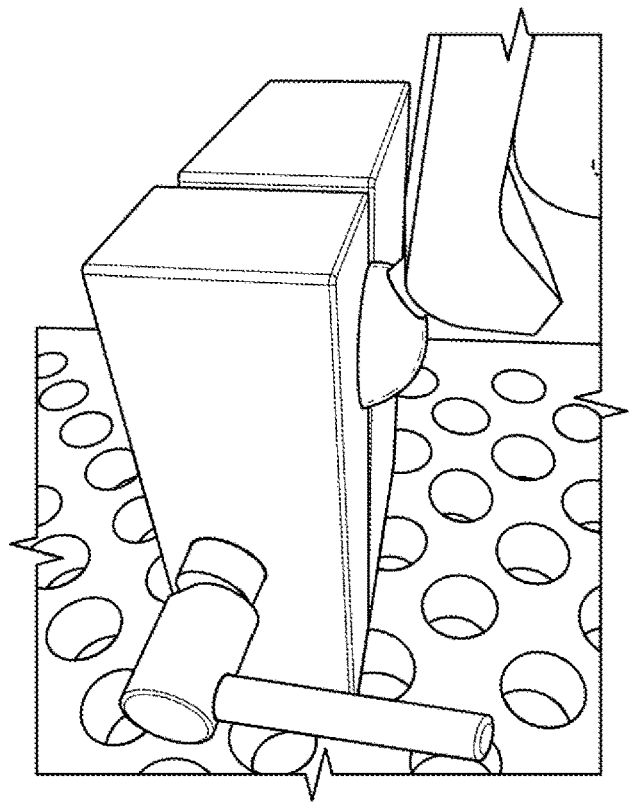

FIG. 27 shows how the pivot system is set up. In FIG. 27, a pegboard is provided. Pivot peg 520 is received within a pegboard hole of the pegboard, generally at a corner of the pegboard, and at least partially supported by main body 510. During use, the patient's acetabulum will be positioned generally close to (or overlaying) the pivot peg 520 such that pivoting the pegboard about the pivot peg pivots of the femur within the generally stationary acetabulum (see FIG. 24D). Additionally, as shown in FIGS. 29A, 29B, and 29C, mounting block 1000 can replace support block 90. Adjustable rotatable tension clamps 1010, 1020 can be used to vary the positioning or orientation of leg positioner 300.

Figure 28A:
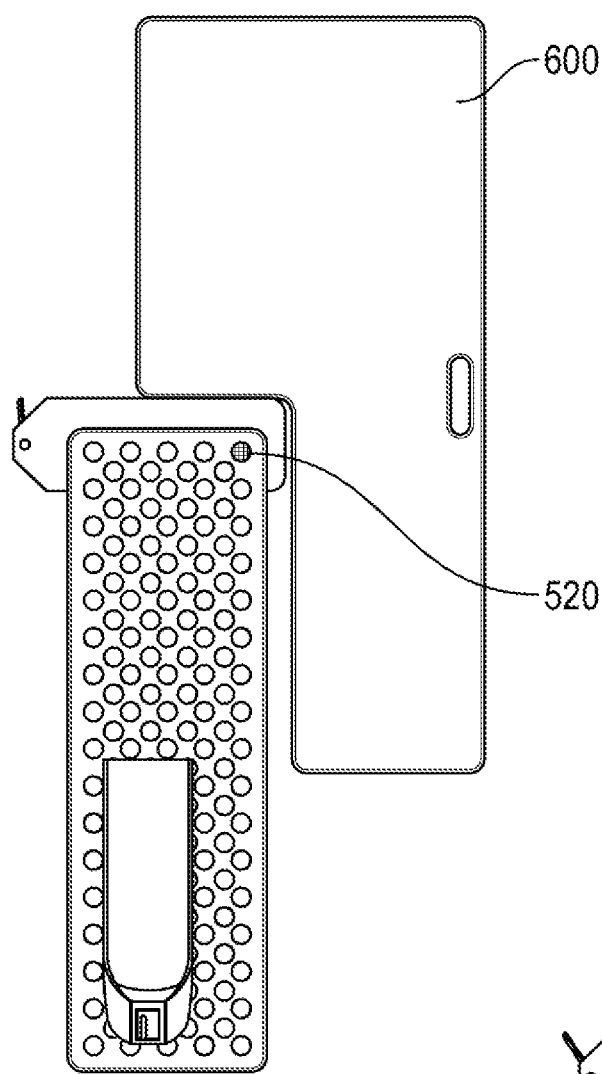
FIGS. 28A and 28B show a first exemplary way of how the pivot system of FIGS. 26, 27 can be used, respectively.

FIGS. 28A, 28B and FIGS. 29A, 29B, show how the pivot system of FIGS. 26, 27 is used. In FIGS. 28A and 29A, the leg pegboard is generally parallel to the longitudinal axis of the main board 600 and therefore the leg to be operated on will also be generally parallel to the axis of the main pegboard as well as the patient's median sagittal plane. The leg to be operated will typically not lie in the plane of the main board 600 (e.g. FIG. 17) because if it were to lie in the plane of the main board 600, it would not be possible for the pivoting pegboard to pivot, because the main board 600 or other leg pegboard would be an obstruction. Note that main board 600 may have pegholes, not have pegholes, or be omitted entirely, wherein the patient's upper body lies directly upon the surgical table.

Figure 28B:
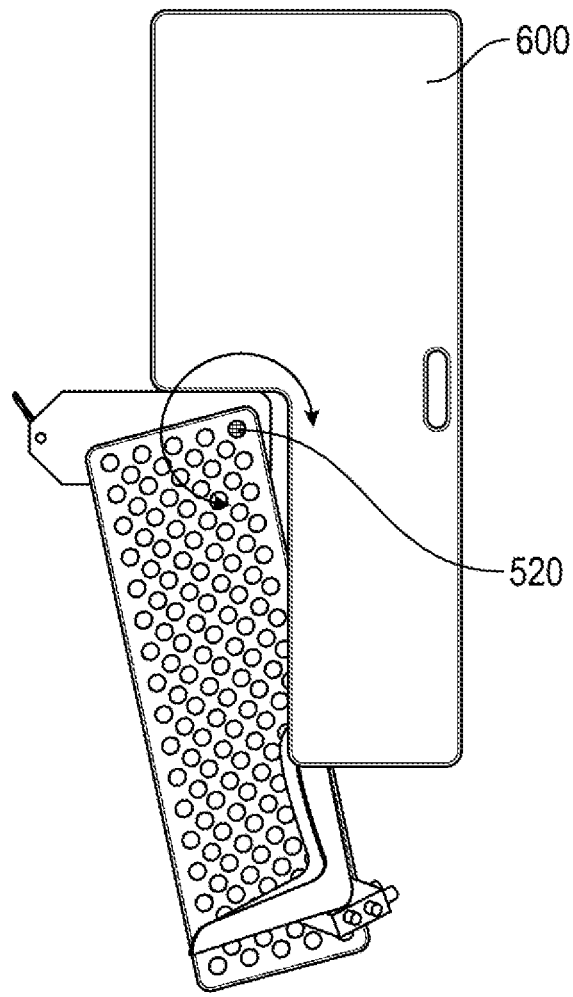
Figure 28C:
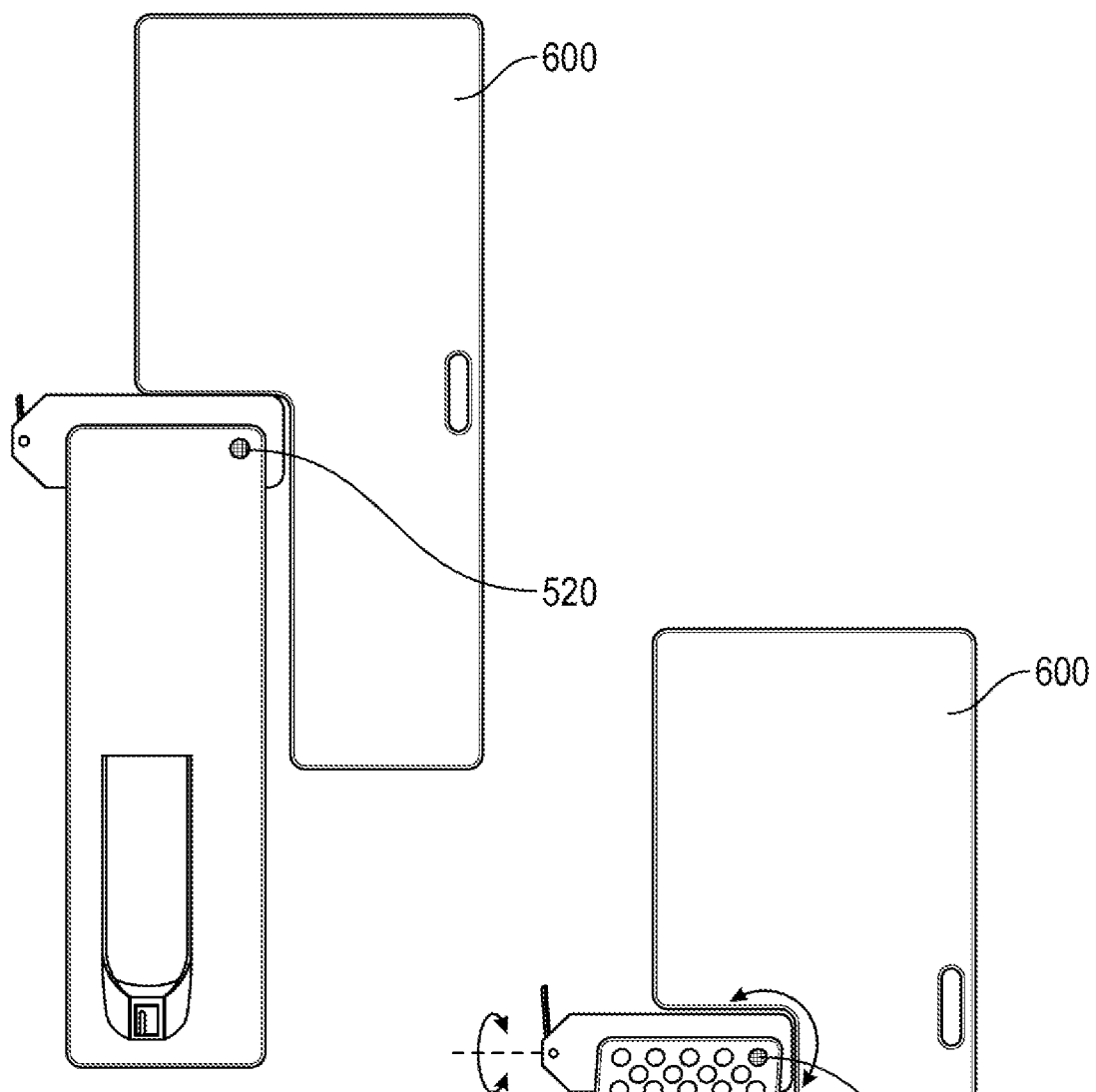
FIG. 28C shows the pivot system of FIGS. 26, 27 in combination with a pivotable board that is not a pegboard.

In FIGS. 28B and 29B, the leg pegboard is pivoted about pivot peg 520 at some desired angle relative to the axis of the main board 600 and the patient's median sagittal plane. Therefore, the leg to be operated on will also be at the desired angle relative to the axis of the main board 600 and the patient's median sagittal plane. Accordingly, the amount of rotation of the femur relative to the acetabulum can be adjusted, resulting in potentially easier surgical procedures. Note that main board 600 may have pegholes, not have pegholes, or be omitted entirely, wherein the patient's upper body lies directly upon the surgical table.

FIGS. 30A, 30B, 30C, and 30D depict an alternative exemplary embodiment for a mounting structure that allows for varying the position or elevation of the knee. In this exemplary embodiment, positioner 1000 with pegs receivable in peg board holes, receives a sphere 1100. Lever 1200 applies or releases a locking grip on sphere 1100. Leg positioner 300 is attached to sphere 1100 through mounting block 90'''. With this exemplary embodiment, a wide range of motion (ROM) of leg positioner 300 is available.

The exemplary embodiments shown and described above are only examples. Therefore, many such details are neither shown nor described. Even though numerous characteristics and advantages of the present technology have been set forth in the foregoing description, together with details of the structure and function of the present disclosure, the disclosure is illustrative only, and changes may be made in the detail, especially in decorative and structural matters of shape, size and arrangement of the parts within the principles of the present disclosure up to, and including the full extent established by the broad general meaning of the terms used in the claims. It will therefore be appreciated that the embodiments described above may be modified within the scope of the claims.

That which is claimed:

1. A modular patient positioning system, comprising:
   at least a first board and a second board, the first board and second board can be rotated relative to each other; wherein:
   at least the second board comprises a second pegboard, the second pegboard having at least one pegboard hole defined in the second pegboard;
   in a first configuration; the first board and second pegboard lie along a common plane; and
   in a second configuration, the first board and second pegboard lie along different planes, whereby first and second parts of a patient's body may be positioned and supported in different planes by having the first board support the patient's first body portion and the second pegboard supports the patient's second body portion, wherein the first body portion comprises an upper body portion and the second body portion comprises a leg receiving portion, the second pegboard being pivotable relative to the first board about a pivot peg placed within a pivot peg hole formed in the second pegboard and positioned adjacent to a corner of the second pegboard such that an interior lateral edge of the second pegboard overlaps the first board; and
   a leg positioner with a mounting structure for mounting the leg positioner on the second pegboard and positioning a leg in a predetermined position relative to the second pegboard, the mounting structure of the leg positioner allows for adjusting at least one of axial rotation, abduction/adduction, elevation/depression, distraction/compression, or flexion/extension of the leg, the leg positioner including a boot.

2. The modular patient positioning system of claim 1, wherein the first board comprises a first pegboard.

3. The modular patient positioning system of claim 1, wherein the first board comprises a surface of a surgical table.

4. The modular patient positioning system of claim 1, wherein:

the mounting structure includes a pivot body having the pivot peg;

whereby the second pegboard can be pivoted about the pivot peg.

5. The modular patient positioning system of claim 4, wherein a patient's acetabulum will be positioned close to the pegboard hole to receive to the pivot peg when the patient is positioned on the second pegboard.

6. The modular patient positioning system of claim 4, wherein the angle of the pivot body relative to the first board changes as the system moves from the first configuration to the second configuration.

7. The modular patient positioning system of claim 1, wherein the pivot peg has a diameter that is greater than a diameter of at least one of the pegboard holes formed in the second pegboard.

* * * * *